(12) United States Patent  
Levy

(10) Patent No.: US 6,475,135 B1  
(45) Date of Patent: Nov. 5, 2002

(54) FINGER-GUIDED SUTURE DEVICE

(75) Inventor: Gil Levy, Tel Aviv (IL)

(73) Assignee: Urogyn Ltd., Tel Aviv (IL)

( * ) Notice: Subject to any disclaimer, the term of this patent is extended or adjusted under 35 U.S.C. 154(b) by 0 days.

(21) Appl. No.: 09/577,974

(22) Filed: May 25, 2000

(51) Int. Cl.$^7$ .............................. A61E 2/02; A61E 5/48; A61B 17/04
(52) U.S. Cl. .......................... 600/30; 128/885; 606/139
(58) Field of Search ................................. 606/145–147, 606/139; 128/885; 600/30

(56) References Cited

U.S. PATENT DOCUMENTS

| | | | |
|---|---|---|---|
| 2,738,790 A | * 3/1956 | Todt, Sr. et al. | 128/898 |
| 4,465,070 A | * 8/1984 | Eguchi | 112/169 |
| 4,726,371 A | 2/1988 | Gibbens | |
| 5,013,292 A | * 5/1991 | Lemay | 128/DIG. 25 |
| 5,152,769 A | * 10/1992 | Baber | 112/169 |
| 5,256,133 A | * 10/1993 | Spitz | 128/DIG. 25 |
| 5,364,408 A | 11/1994 | Gordon | |
| 5,423,795 A | 6/1995 | Eckert et al. | |
| 5,458,609 A | 10/1995 | Gordon et al. | |
| 5,520,700 A | * 5/1996 | Beyar et al. | 606/139 |
| 5,540,704 A | 7/1996 | Gordon et al. | |
| 5,575,800 A | 11/1996 | Gordon | |
| 5,578,044 A | 11/1996 | Gordon et al. | |
| 5,603,718 A | * 2/1997 | Xu | 112/169 |
| 5,647,836 A | * 7/1997 | Blake et al. | 600/30 |
| 5,662,664 A | 9/1997 | Gordon et al. | |
| 5,700,272 A | 12/1997 | Gordon et al. | |
| 5,713,910 A | 2/1998 | Gordon et al. | |
| 5,741,277 A | 4/1998 | Gordon et al. | |
| 5,741,279 A | 4/1998 | Gordon et al. | |
| 5,925,064 A | 7/1999 | Meyers et al. | |
| 5,980,538 A | * 11/1999 | Fuchs et al. | 606/139 |
| 6,039,686 A | * 3/2000 | Kovac | 600/30 |
| 6,048,351 A | 4/2000 | Gordon et al. | |
| 6,050,937 A | * 4/2000 | Benderev | 600/30 |
| 6,117,067 A | * 9/2000 | Gil-Vernet | 128/DIG. 25 |

FOREIGN PATENT DOCUMENTS

WO 98/00069 1/1998

* cited by examiner

*Primary Examiner*—Gary Jackson  
(74) *Attorney, Agent, or Firm*—G.E. Ehrlich Ltd.

(57) ABSTRACT

A finger-guided suture device is disclosed. The device includes a thimble-like element to surround a portion of a finger and an ejectable substantially semi-circular surgical needle for collecting retaining and guiding a surgical suture via a distal portion of the needle upon contact. Also included is a mechanism for ejecting the needle from, and withdrawing the needle into, the thimble-like element, so as to place a suture. Also disclosed are surgical methods employing the device.

37 Claims, 32 Drawing Sheets

FINGER-GUIDED SUTURE DEVICE

FIELD AND BACKGROUND OF THE INVENTION

The present invention relates to suture devices, and more particularly, to a finger-guided suture device for placing sutures especially in body locations of limited minimal-invasive accessibility. The present invention further relates to surgical procedures in which one or more finger-guided suture devices of the present invention are used to place one or more sutures, especially in body locations of limited minimal-invasive accessibility.

For years, there has been a discernible, clear tendency in surgery and invasive diagnosis, especially, but not exclusively, in abdominal, joint, vaginal, in-utero and brain, surgeries or diagnoses, to develop procedures that would reduce the need for major access-providing incisions with their concomitant requirements of general anesthesia, extended hospitalization and increased infection hazard. One step in this direction was the introduction of endoscopy and laparoscopy, which, through provision of minimal incision in, e.g., the abdominal wall of joint covering skin, permits the introduction into the abdominal cavity or joint of a miniature television camera including a light source, as well as of various surgical instruments, including suture devices.

PCT/US97/11494 teaches a number of surgical instruments which can be mounted directly on a surgeon's fingertip in a way that the surgeon can insert his or her hand into a natural cavity of the patient or through a minimal incision to perform surgical procedures, and also to use his or her fingers to manipulate tissues, thus enabling the surgeon to perform the procedures with the benefits of minimally invasive surgery, but with much greater tactile sense, control, and ease of manipulation. However, these surgical instruments (i) are carried by a finger and operated by the thumb, thereby are not applicable for procedures in which a single finger is employed for tactile sensing an operated intrabody location; (ii) include an operating head which permanently extends far beyond the fingertip on which the surgical instrument is mounted, which limits the tactile sensing of the surgeon; and/or (iii) prevent tactile sensing by the instrument carrying fingertip altogether.

According to the teachings of PCT/US97/11494 suturing can be performed while the surgeon uses tactile information collected by a single fingertip for tactile sensing the intrabody site to be stitched prior to the actual suturing. Several non-limiting examples of such suturing procedures are described in detail in the sections that follow. However, once the surgeon has collected the tactile information, surgery is conducted blindly within the body of the patient. According to the teachings of PCT/US97/11494, both the hands of the surgeon are engaged. Evidently, blindly operating surgical instruments intrabodily based on finger tip tactile information collected earlier may prove inconvenient, inaccurate and may increase the chance of inadvertently harming the patient.

PCT/IL99/00084 teaches design of finger-guided suture devices which can be used to perform extra- as well as intrabody suturing of tissue. This application does not teach construction and use of a device which causes a needle to penetrate a bodily tissue engage a piece of suture material and pull the suture material through the bodily tissue as the needle is retracted there through. In addition, this application fails to teach a construction which allows safe withdrawal of the needle in case of early detected misplacement other than pulling it via the hand or suture.

There is thus a widely recognized need for, and it would be highly advantageous to have, finger-guided suture devices devoid of the limitations associated with the prior art instruments and which enable a surgeon using a finger-guided surgical device to penetrate a bodily tissue with a suture needle, engage a piece of suture material with the needle and pull the suture material through the bodily tissue as the needle is retracted there through.

SUMMARY OF THE INVENTION

According to one aspect of the present invention there is provided a finger-guided suture device. The device comprises (a) a thimble-like element being adapted to surround a portion of a surgeon's finger; (b) a rotatably mounted substantially semi-circular surgical needle within a housing formed within, or connected to, a wall of the thimble-like element, the surgical needle being designed for collecting the surgical suture via a distal portion of the surgical needle upon contact therewith and for retaining and guiding the surgical suture while suturing; and (c) a mechanism for imparting to said surgical needle a rotary movement in one direction for ejecting the surgical needle from the thimble-like element and thereafter a rotary movement in the opposite direction for withdrawing the surgical needle into the thimble-like element, so as to place a suture.

According to another aspect of the present invention there is provided a surgical procedure for bladder-neck suspension for treatment of urinary incontinence, the procedure comprising the step of suspending a pelvic fascia and a vaginal wall lateral to a urethra of a patient to Cooper's ligament by a surgical suture applied by using a finger-guided suture device having a rotatably-driven substantially semi-circular surgical needle designed for collecting the surgical suture via a distal portion of the surgical needle upon contact therewith and for retaining and guiding the surgical suture while suturing.

According to yet another aspect of the present invention there is provided a surgical procedure for treatment of rectal prolapse, the procedure comprising the step of constricting an anal opening by a surgical suture applied by using a finger-guided suture device having a rotatably-driven, substantially semi-circular surgical needle designed for collecting the surgical suture via a distal portion of the surgical needle upon contact therewith and for retaining and guiding the surgical suture while suturing.

According to still another aspect of the present invention there is provided a surgical procedure for treatment of esophageal reflux, the procedure comprising the step of positioning a vessel loop around a esophagus of a patient by a surgical suture applied by using a finger-guided suture device having a rotatably-driven, substantially semi-circular surgical needle designed for collecting the surgical suture via a distal portion of the surgical needle upon contact therewith and for retaining and guiding the surgical suture while suturing.

According to an additional aspect of the present invention there is provided a surgical procedure for treatment of vaginal prolapse, the procedure comprising the step of tying an upper part of a vagina of a patient to a sacrospinous ligament of the patient by a surgical suture applied by using a finger-guided suture device having rotatably-driven, substantially semi-circular surgical needle designed for collecting the surgical suture via a distal portion of the surgical needle upon contact therewith and for retaining and guiding the surgical suture while suturing.

According to yet additional aspect of the present invention there is provided a surgical procedure for treatment of rupture of a rectum in large animals, the procedure comprising the step of suturing the rupture by a surgical suture applied by using a finger-guided suture device having a rotatably-driven, substantially semi-circular surgical needle designed for collecting the surgical suture via a distal portion of the surgical needle upon contact therewith and for retaining and guiding the surgical suture while suturing.

According to still additional aspect of the present invention there is provided a surgical procedure for treatment of rupture of a cervix in large animals, the procedure comprising the step of suturing the rupture by a surgical suture applied by using a finger-guided suture device having a rotatably-driven, substantially semi-circular surgical needle designed for collecting the surgical suture via a distal portion of the surgical needle upon contact therewith and for retaining and guiding the surgical suture while suturing.

According to still additional aspect of the present invention there is provided a surgical procedure for treatment of rupture of a uterus in large animals, the procedure comprising the step of suturing the rupture by a surgical suture applied by using a finger-guided suture device having a rotatably-driven, substantially semi-circular surgical needle designed for collecting the surgical suture via a distal portion of the surgical needle upon contact therewith and for retaining and guiding the surgical suture while suturing.

According to further features in preferred embodiments of the invention described below, the thimble like element is designed and constructed to expose the ventral tactile portions of the distal phalanx of the surgeon's finger, so as to enable the surgeon to tactile sense a body location to be sutured.

According to still further features in the described preferred embodiments, the finger-guided suture device further comprises a cartridge for holding the surgical suture and presenting it for collection by the distal portion of the surgical needle.

According to still further features in the described preferred embodiments the cartridge includes at least one mechanism designed and constructed, so as to maintain a predetermined tension of the surgical suture.

According to still further features in the described preferred embodiments the at least one mechanism designed and constructed, so as to maintain a predetermined tension of the surgical suture comprises at least one piece of flexible material containing at least one hole through which the surgical suture passes.

According to still further features in the described preferred embodiments the at least one piece of flexible material containing at least one hole is selected from the group consisting of a single piece of flexible material containing two holes and a pair of pieces of flexible material each containing one hole.

According to still further features in the described preferred embodiments the flexible material is selected from the group consisting of silicon, latex, rubber, fabric, and fabric with an eyelet.

According to still further features in the described preferred is embodiments the eyelet is constructed of material selected from the group consisting of silicon, latex, rubber and fabric.

According to still further features in the described preferred embodiments the mechanism for ejecting the surgical needle from, and withdrawing the surgical needle into, the thimble-like element, is selected from the group consisting of a belt actuated mechanism, a gear actuated mechanism and a combined gear and belt actuated mechanism.

According to still further features in the described preferred embodiments the surgical needle is formed with a feature selected from the group consisting of a notch, a hook, at least one arm, and an openable loop at the distal end thereof.

According to still further features in the described preferred embodiments the finger-guided suture device further comprises an adapter insertable between the thimble-like element and the surgeon's finger, so as to adapt the suture device to fingers of different size.

According to still further features in the described preferred embodiments the mechanism includes a first portion engaged within the housing and which is in contact with the ejectable surgical needle and a second, remote, portion which is to extend out of the patient's body and which is operable by a free hand of the surgeon so as to eject the surgical needle from the thimble-like element.

According to still further features in the described preferred embodiments the first portion of the mechanism comprises a rotatable wheel having an axle, the axle serves for engaging the surgical needle and imparting a rotational motion in at least one direction thereto, the surgical needle includes a mechanism for engaging the rotatable wheel and a locking piece for insuring that the surgical needle and the rotatable wheel remain engaged.

According to still further features in the described preferred embodiments the first portion of the mechanism comprises a rotatable wheel having a mechanism for engaging a drive arm and imparting a rotational motion in at least one direction thereto, the drive arm is designed and constructed engageable by the rotatable wheel and by the surgical needle and to impart a rotational motion of the rotatable wheel in at least one direction to the surgical needle, wherein the surgical needle further includes a mechanism for engaging the drive arm and a disk for ensuring that the surgical needle, the drive arm and the rotatable wheel remain engaged.

According to still further features in the described preferred embodiments the remote portion which is to extend out of the patient's body and which is operable by a free hand of the surgeon so as to eject the surgical needle from the thimble-like element comprises: (i) a hand operable actuator designed and constructed to operate a drive mechanism; (ii) a drive housing for containing at least a portion of the drive mechanism; and (iii) at least a portion of the drive mechanism, the drive mechanism being for imparting a rotational motion in at least one direction to the surgical needle.

According to still further features in the described preferred embodiments the hand operable actuator of the remote portion comprises (1) a handle for engaging at least one finger of the free hand of the surgeon; (2) an extending piece containing a plurality of arcurate teeth and being movable through the drive housing; (3) a pressure sensitive spring; and (4) a brake handle, the brake handle operable in a first direction by the pressure sensitive spring and in a second direction by the at least one finger of the free hand of the surgeon.

According to still further features in the described preferred embodiments the drive mechanism comprises (1) a plurality of arcuate is teeth deployed in a linear arrangement along an extending piece of a handle; (2) a first gear with a first circular arrangement of arcuate teeth, the first circular arrangement of arcuate teeth being for engaging with the plurality of arcuate teeth deployed in the linear arrangement along the extending piece, such that linear displacement of the extending piece is translated into rotational motion of the first gear; (3) a second gear including a second circular arrangement of arcuate teeth, the arcuate teeth of the second gear being for engaging the first circular arrangement of arcuate teeth of the first gear, such that rotational motion of the first gear causes rotational motion of the second gear; and (4) a cable in contact with at least one point on the second gear, such that rotational motion of the second gear is translated to linear motion of at least a portion of the cable.

According to still further features in the described preferred embodiments the drive mechanism further comprises (5) a ratchet for alternately engaging and releasing at least one arcuate tooth of the first gear; (6) a ratchet control arm for alternately engaging and releasing the ratchet; (7) a brake handle for alternately operating the ratchet control arm. These components are arranged so that when the brake handle operates the ratchet control arm, the ratchet control arm releases the ratchet, the ratchet engages the at least one arcuate tooth of the first gear and the first gear is prevented from rotating. This means that when the brake handle does not operate the ratchet control arm, the ratchet control arm engages the ratchet, the ratchet releases the at least one arcuate tooth of the first gear and the first gear is free to rotate.

According to still further features in the described preferred embodiments the thimble-like element is constructed so as to be mounted over a dorsal side of the distal phalanx of the surgeon's finger, thereby exposing the entire ventral tactile portions of the distal phalanx.

According to still further features in the described preferred embodiments the thimble-like element is constructed so as to fully surround the distal phalanx and expose the tip of the ventral tactile portion of the distal phalanx.

According to still further features in the described preferred embodiments the thimble-like element is constructed so as to be mounted over a ventral side of the distal phalanx of the surgeon's finger and expose the tip of the ventral tactile portion of the distal phalanx.

According to still further features in the described preferred embodiments the surgical needle is ejectable in a direction generally perpendicular to a longitudinal axis of the thimble like element.

According to still further features in the described preferred embodiments the surgical needle travels along at least a portion of a circular path, the path being on a plane which substantially parallels a plane traversing the surgeon's finger from top to bottom.

According to still further features in the described preferred embodiments the surgical needle travels along at least a portion of a circular path, the path being on a plane which substantially parallels a plane traversing the surgeon's finger from side to side.

According to still further features in the described preferred embodiments the surgical needle travels along at least a portion of a circular path, the path being on a plane which is substantially perpendicular to the longitudinal axis of the surgeon's finger.

According to still further features in the described preferred embodiments the finger-guided suture device further comprises an optical head engaged by the thimble like element.

According to still further features in the described preferred embodiments the finger-guided suture device further comprises the surgical suture formed with a loop for collection by the surgical needle.

According to still further features in the described preferred embodiments the wall is a side wall of the thimble-like element.

According to still further features in the described preferred embodiments the wall is a front wall of the thimble-like element.

According to still further features in the described preferred embodiments the finger-guided suture device further comprises a reporting mechanism for reporting at least one situation selected from the group consisting of a full ejection of the substantially semi-circular surgical needle, a full withdrawal of the substantially semi-circular surgical needle, a degree of ejection of the substantially semi-circular surgical needle and a degree of withdrawal of the substantially semi-circular surgical needle.

The present invention successfully addresses the shortcomings of the presently known configurations by providing a finger guided suture including a needle which is capable of collecting the surgical suture via a distal portion of the surgical needle upon contact therewith and retaining and guiding the surgical suture while suturing.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
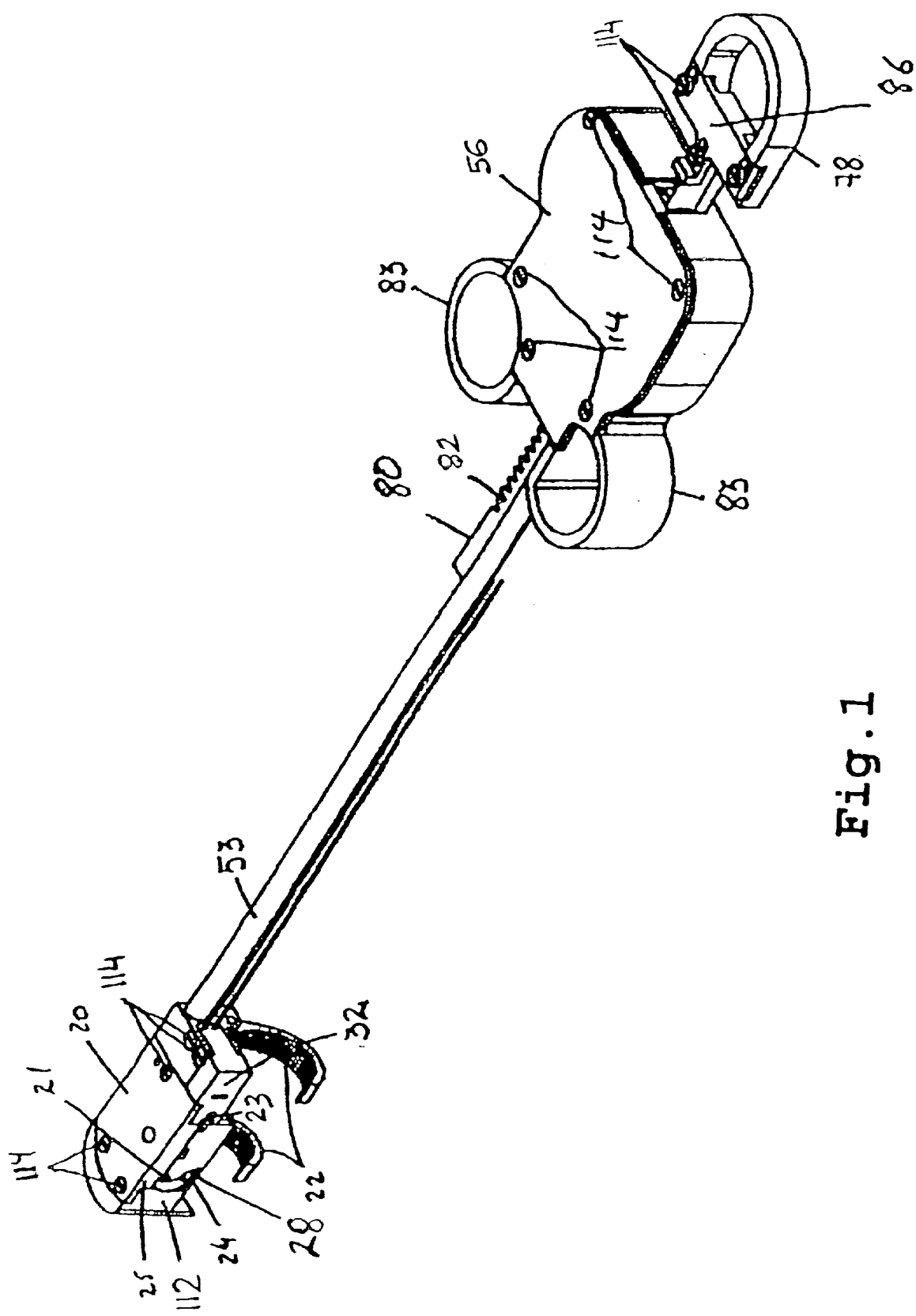
FIG. 1 is a perspective view of one embodiment of a finger-guided suture device according to the present invention including an external actuation device.

The present invention is of a finger-guided suture device which can be used to place sutures, especially in body locations of limited minimal-invasive accessibility and further to surgical procedures employing the device. Specifically, the present invention can be used to allow a surgeon while tactilely sensing an intrabodily location to collect surgical suture via a distal portion of a surgical needle upon contact therewith and retain and guide the surgical suture while suturing.

The principles and operation of a finger guided suture device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
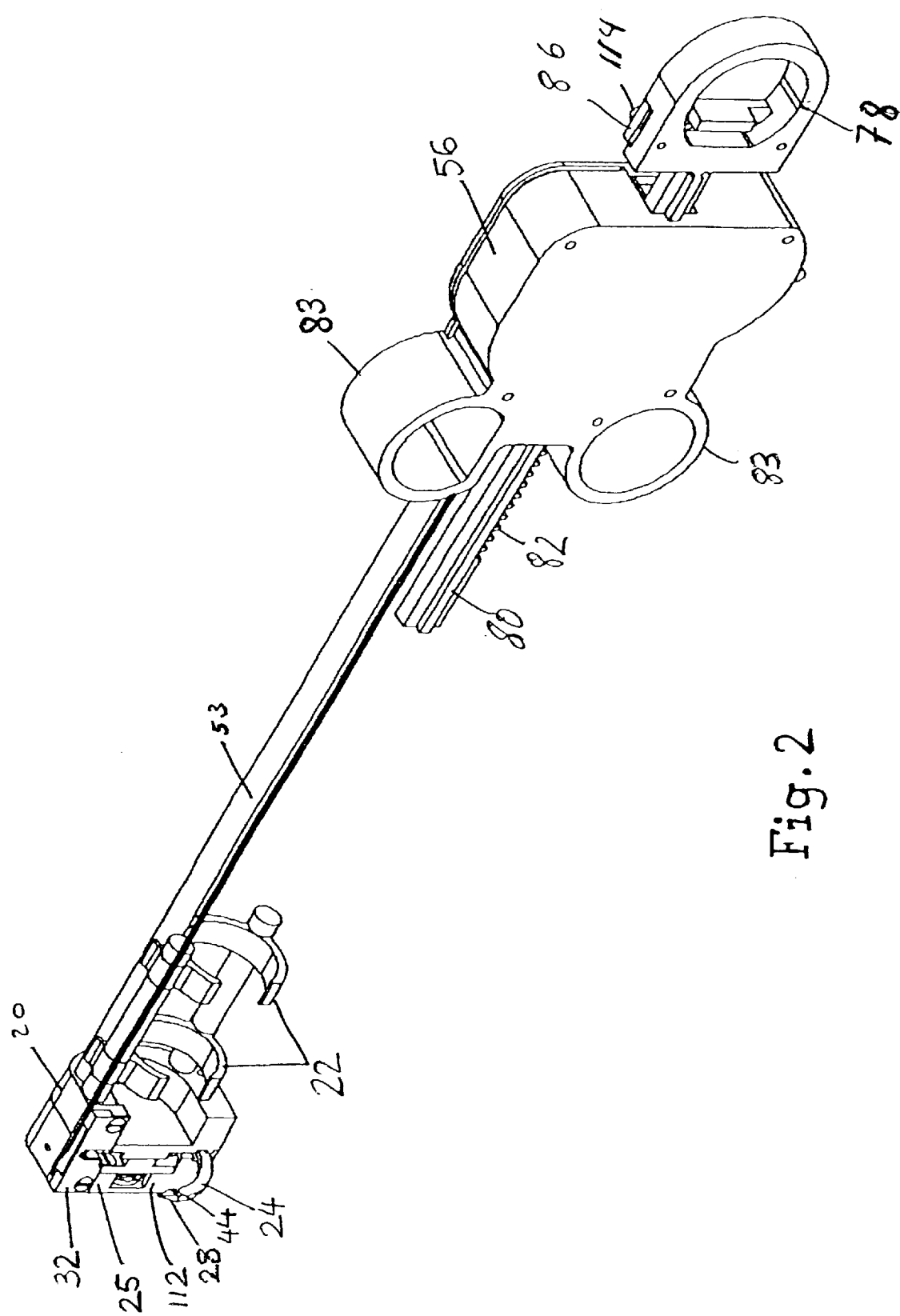
FIG. 2 is a perspective view of a second embodiment of a finger-guided suture device according to the present invention including an external actuation device.

In the drawings two embodiments of a finger-guided suture device, which is referred to herein below as device 20, are pictured (FIGS. 1 and 2). The preferred embodiments of the device depicted in FIG. 1 are further detailed in FIGS. 3–10, while the preferred embodiments of the device depicted in FIG. 2 are further detailed in FIGS. 11–20.

Device 20 includes a thimble like element 22, a surgical needle 24, and a mechanism 30 for driving needle 24 in order to form a suture. Mechanism 30 is divided into a first portion 54 (FIGS. 3 and 12) and a second remote portion 56 in the two pictured embodiments of device 20. Remote portion 56 of drive mechanism 30 is detailed in FIGS. 21–30. The two portions 54 and 56 of mechanism 30 are connected by a pipe or tube 53 containing a cable 100 (FIGS. 4 and 15) which serves to drive needle 24.

Figure 32A:
FIGS. 32a–b are of adapters for use with a thimble like element according to the present invention.
Figure 32B:
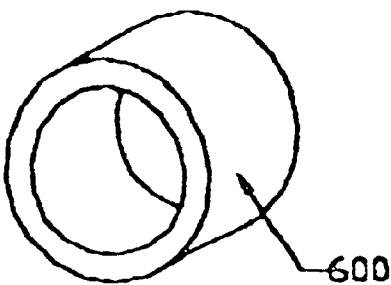
Figure 33:
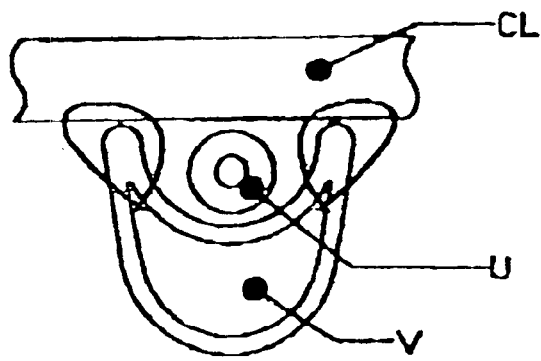
FIG. 33 is a schematic representation of the vagina and the urethra after a surgical procedure is completed using a device according to the present invention. (v is vagina, s is suture, U is Urethra and CL is Cooper's Ligament)

Thimble-like element 22 (FIGS. 8, 9, 10, 17, 18, and 19) is adapted to surround a portion of a surgeon's finger. Thimble-like element 22 is constructed to expose the ventral tactile portions of the distal phalanx of the surgeon's finger, so as to enable the surgeon to tactile sense a body location to be sutured (FIGS. 4, 6, 8, 9, 15, 17 and 18). In the preferred embodiments of FIGS. 11, 15, 17, 18 and 19 thimble-like element 22 is constructed so as to be mounted over a dorsal side of the distal phalanx of the surgeon's finger, thereby exposing the entire ventral tactile portions of the distal phalanx. In the preferred embodiment pictured in FIGS. 4, 8, and 9, thimble-like element 22 is constructed so as to fully surround the distal phalanx and expose the tip of the ventral tactile portion of the distal phalanx such that it can be mounted over a ventral side of the distal phalanx of the surgeon's finger and expose the tip of the ventral tactile portion of the distal phalanx. Device 20 may further include an adapter 600 insertable between the thimble-like element 22 and the surgeon's finger, so as to adapt the suture device to fingers of different size (FIGS. 32a–b).

Figure 31A:
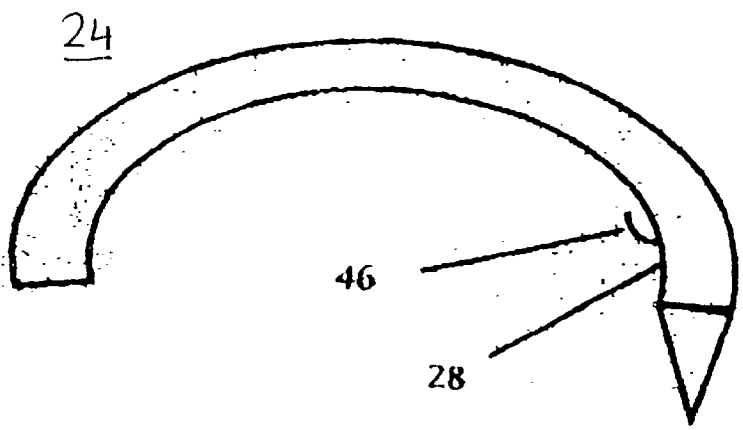
FIGS. 31a–c show a hook, at least one arm, and an openable loop at a distal end of the surgical needle.
Figure 31B:
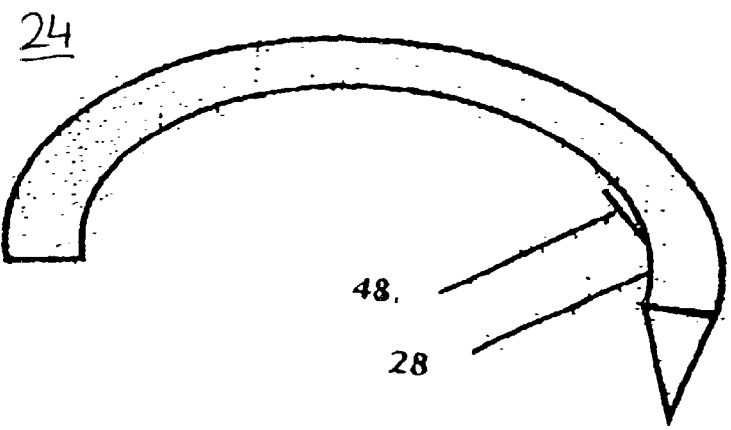
Figure 31C:
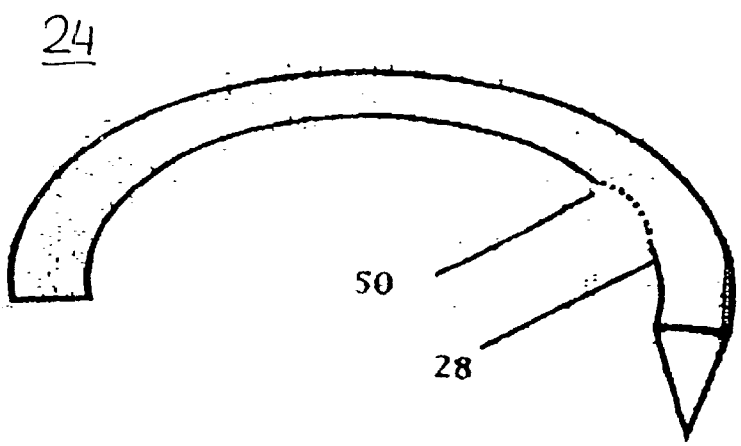

Surgical needle 24 is an ejectable substantially semi-circular needle engaged within a housing 25 being formed within, or connected to, a wall 112 of thimble-like element 22. Wall 112 may be, for example a sidewall (FIG. 1) or a front wall (FIG. 2) of thimble like element 22. Needle 24 is designed for collecting a surgical suture 26 via a distal portion 28 of needle 24 upon contact with suture 26 and for retaining and guiding suture 26 while suturing. Suture 26 is collected retained and guided by, for example, notch 44 of needle 24. The function of notch 44 may be performed equally well by, for example, a hook 46, at least one arm 48, or an openable loop 50 at distal end 28 of needle 24 (FIGS. 31 a, b and c).

According to a preferred embodiment of the present invention surgical needle 24 is ejectable in a direction generally perpendicular to a longitudinal axis of thimble like element 22 (FIGS. 11–20).

According to another preferred embodiment of the present invention surgical needle 24 travels along at least a portion of a circular path, the path being on a plane which substantially parallels a plane traversing the surgeon's finger from top to bottom (FIGS. 11–20).

According to yet another preferred embodiment of the present invention surgical needle 24 travels along at least a portion of a circular path, the path being on a plane which substantially parallels a plane traversing the surgeon's finger from side to side (FIGS. 3–10).

According to still another preferred embodiment of the present invention surgical needle 24 travels along at least a portion of a circular path, the path being on a plane which is substantially perpendicular to the longitudinal axis of the surgeon's finger (FIGS. 3–10).

Mechanism 30 serves for ejecting surgical needle 24 from housing 25 formed in thimble-like element 22 via an exit point 21 and thereafter withdrawing surgical needle 24 into housing 25 of thimble-like element 22 via an entry point 23, so as to place a suture. Distal portion 28 of needle 24 collects suture 26 after passing through entry point 23 by engaging a loop 110 of suture 26 in a notch 44 formed at a distal end of needle 24. In the pictured embodiments of device 20, needle 24 is then withdrawn back through entry point 23 and into exit point 21 placing a suture. Mechanism 30 may be, for example, a belt actuated mechanism, a gear actuated mechanism or a combined gear and belt actuated mechanism (as depicted in the drawings). More details of the alternative preferred embodiments of mechanism 30 are further described hereinbelow.

Figure 6:
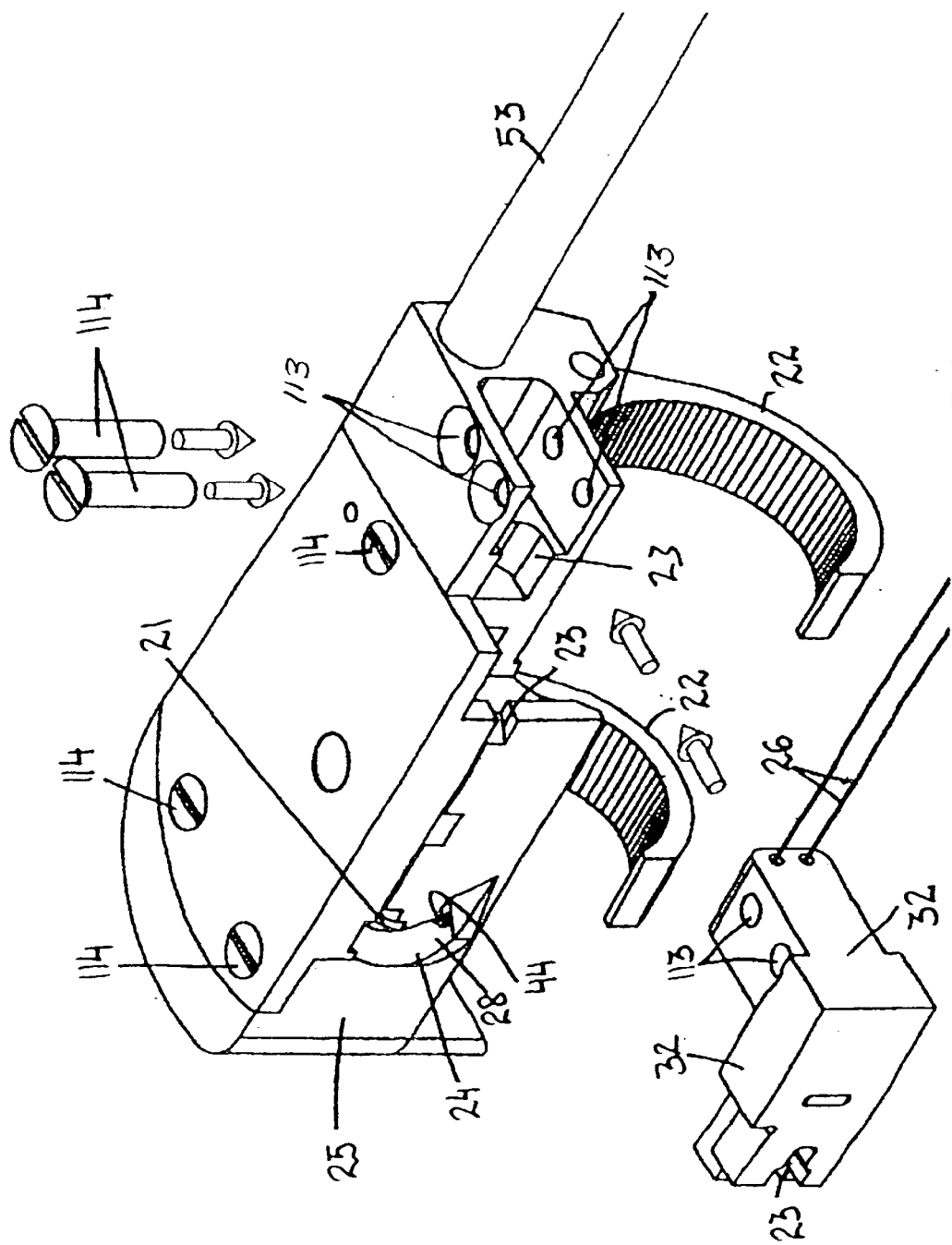
FIG. 6 shows the assembly of the cartridge to a thimble like element according to the embodiment of the finger-guided suture device depicted in FIG. 1.
Figure 7:
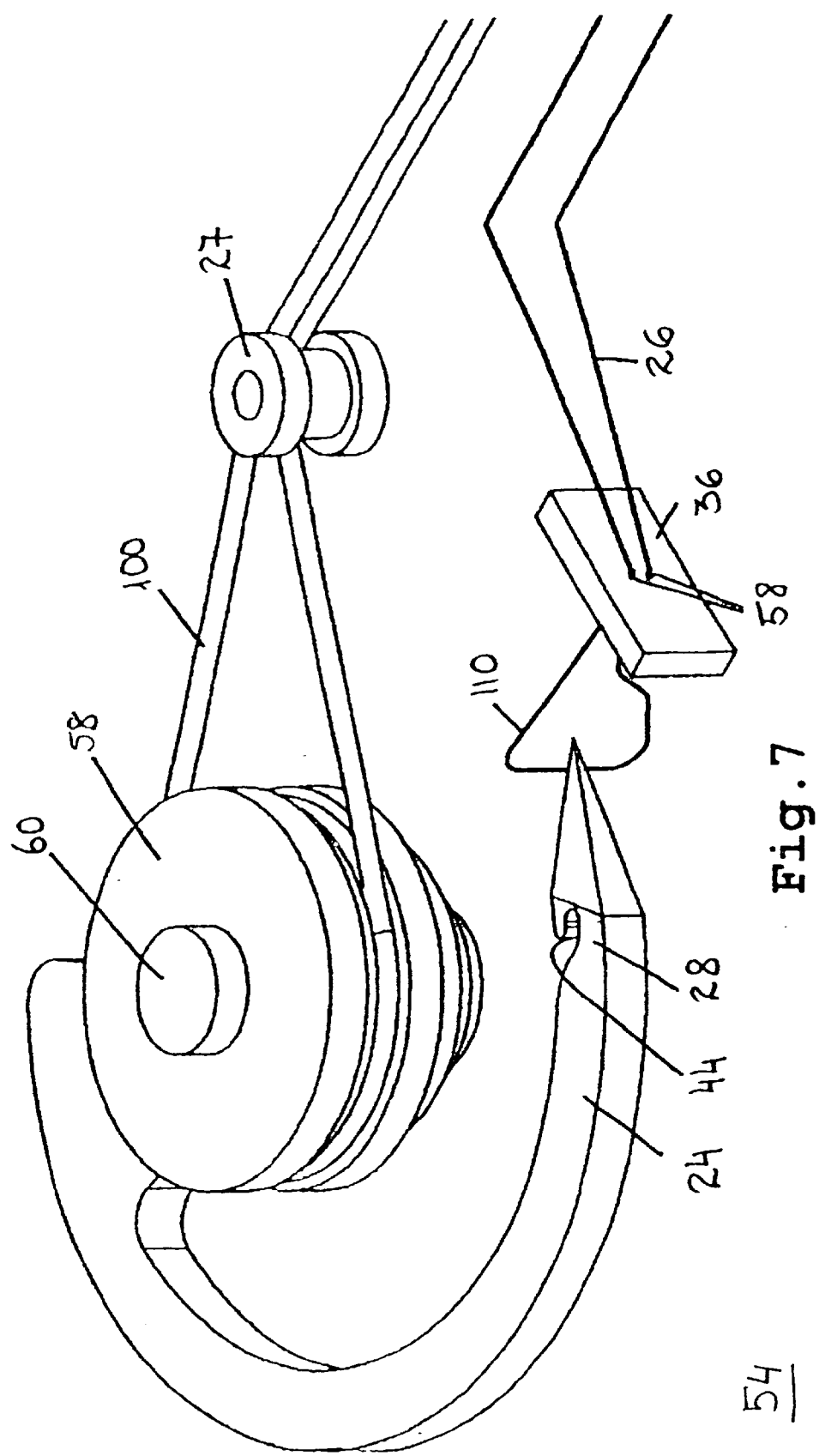
FIG. 7 shows how a surgical suture may be engaged by a surgical needle according to the embodiment of the finger-guided suture device depicted in FIG. 1.
Figure 8:
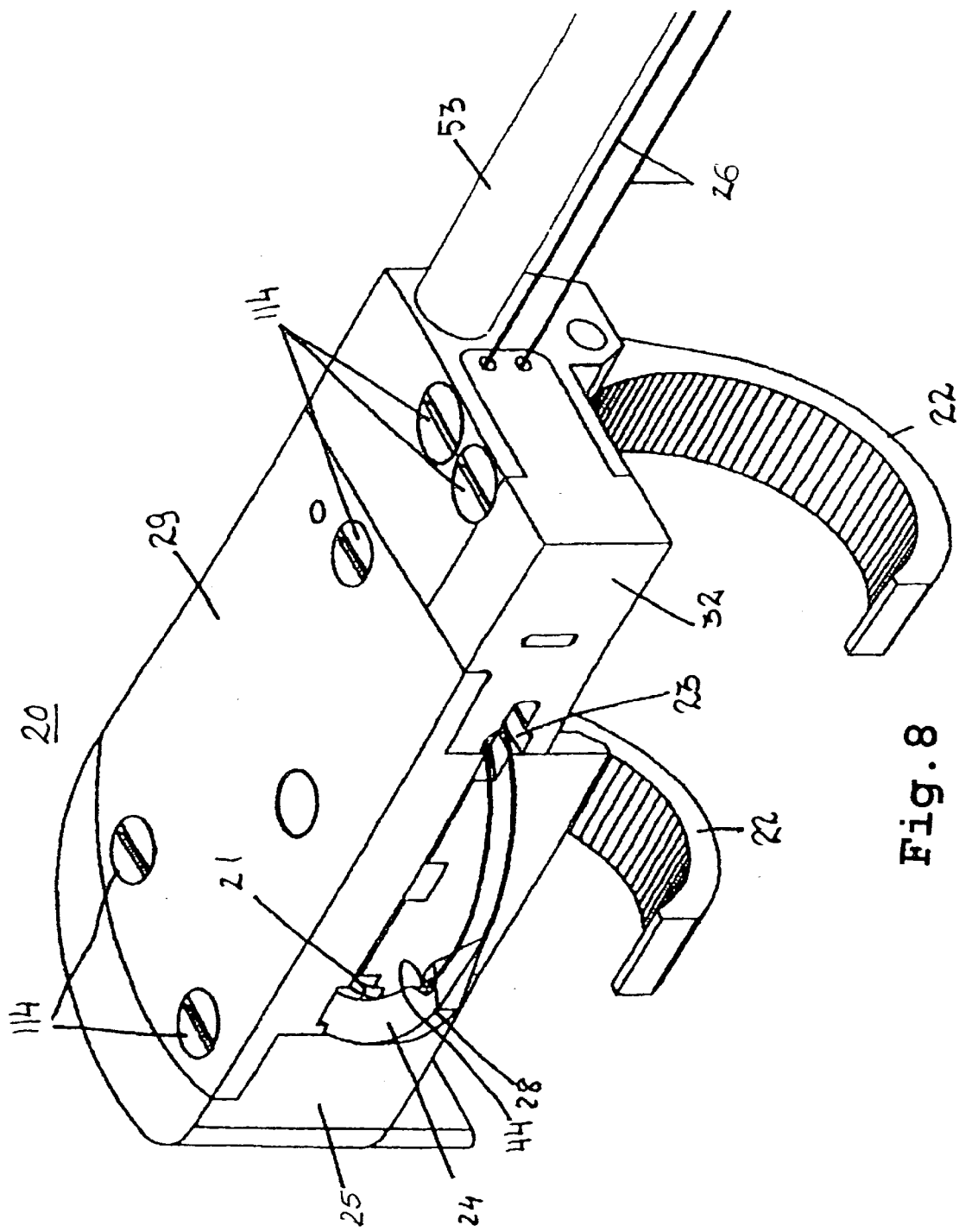
FIG. 8 is a perspective view of the finger-guided suture device according to the embodiment depicted in FIG. 1 in which engagement of a suture by the needle is depicted.
Figure 9:
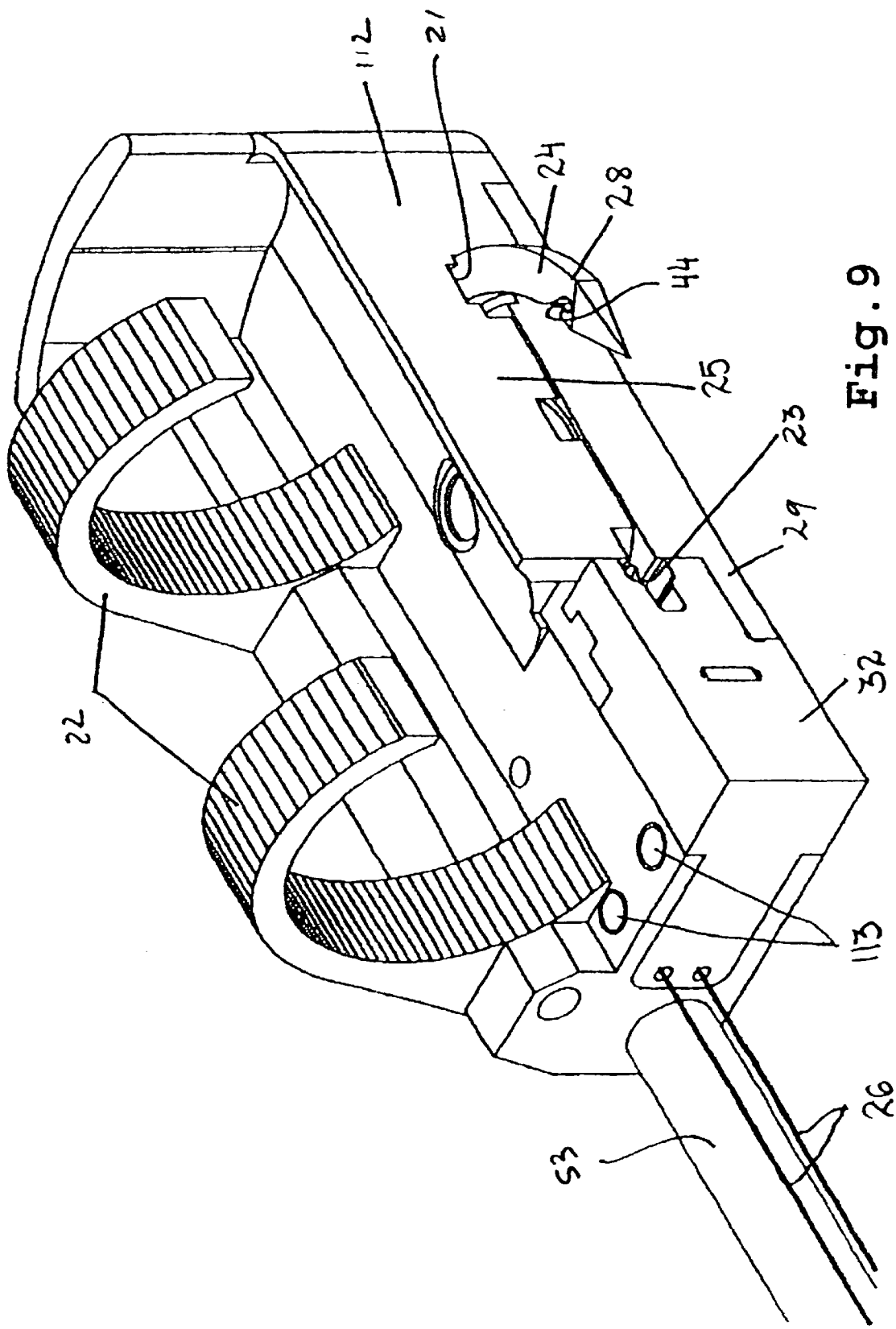
FIG. 9 is an underside perspective view of the finger-guided suture device according to the embodiment depicted in FIG. 1.
Figure 10:
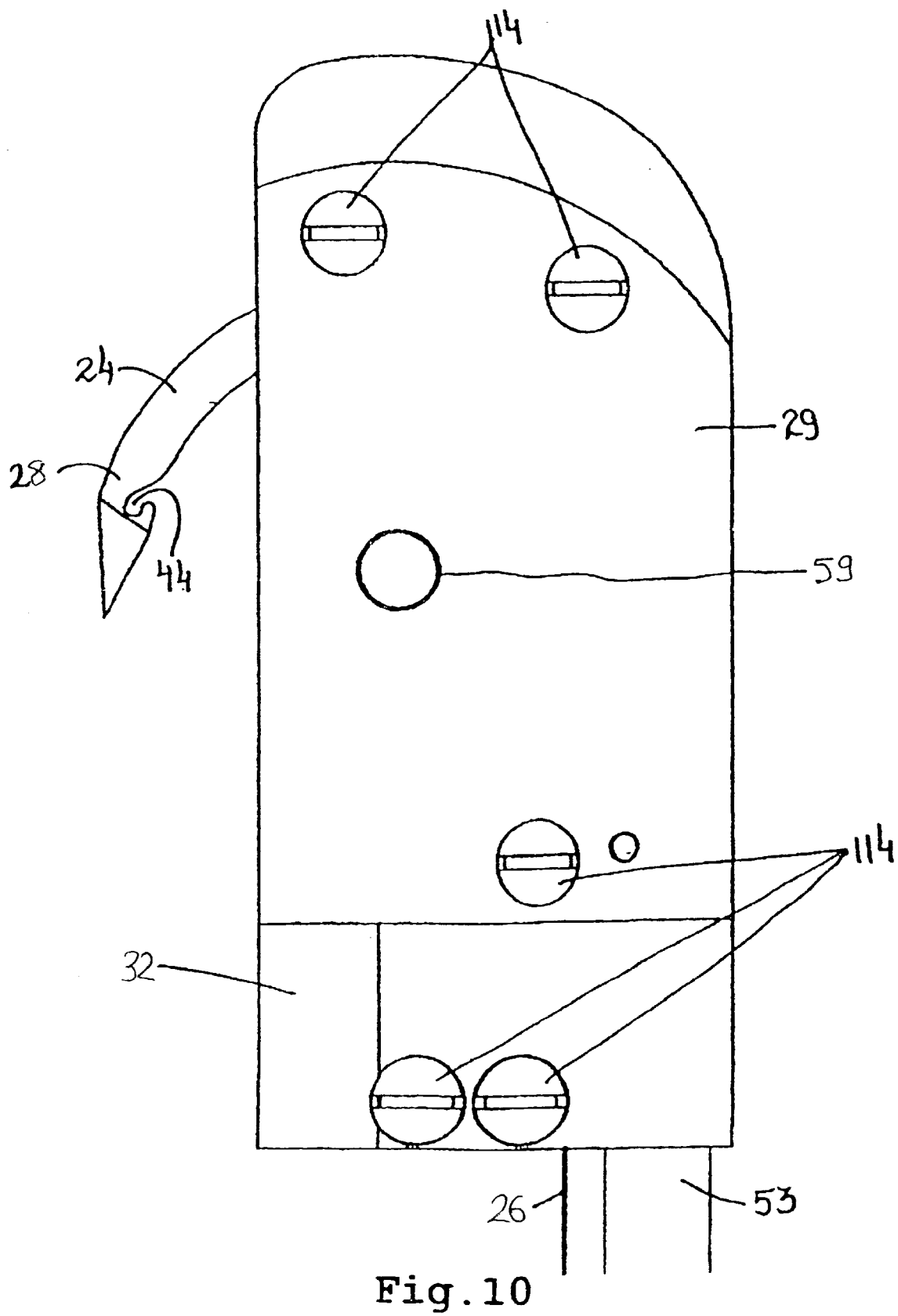
FIG. 10 is a top view of a finger-guided suture device according to the embodiment depicted in FIG. 1.
Figure 11:
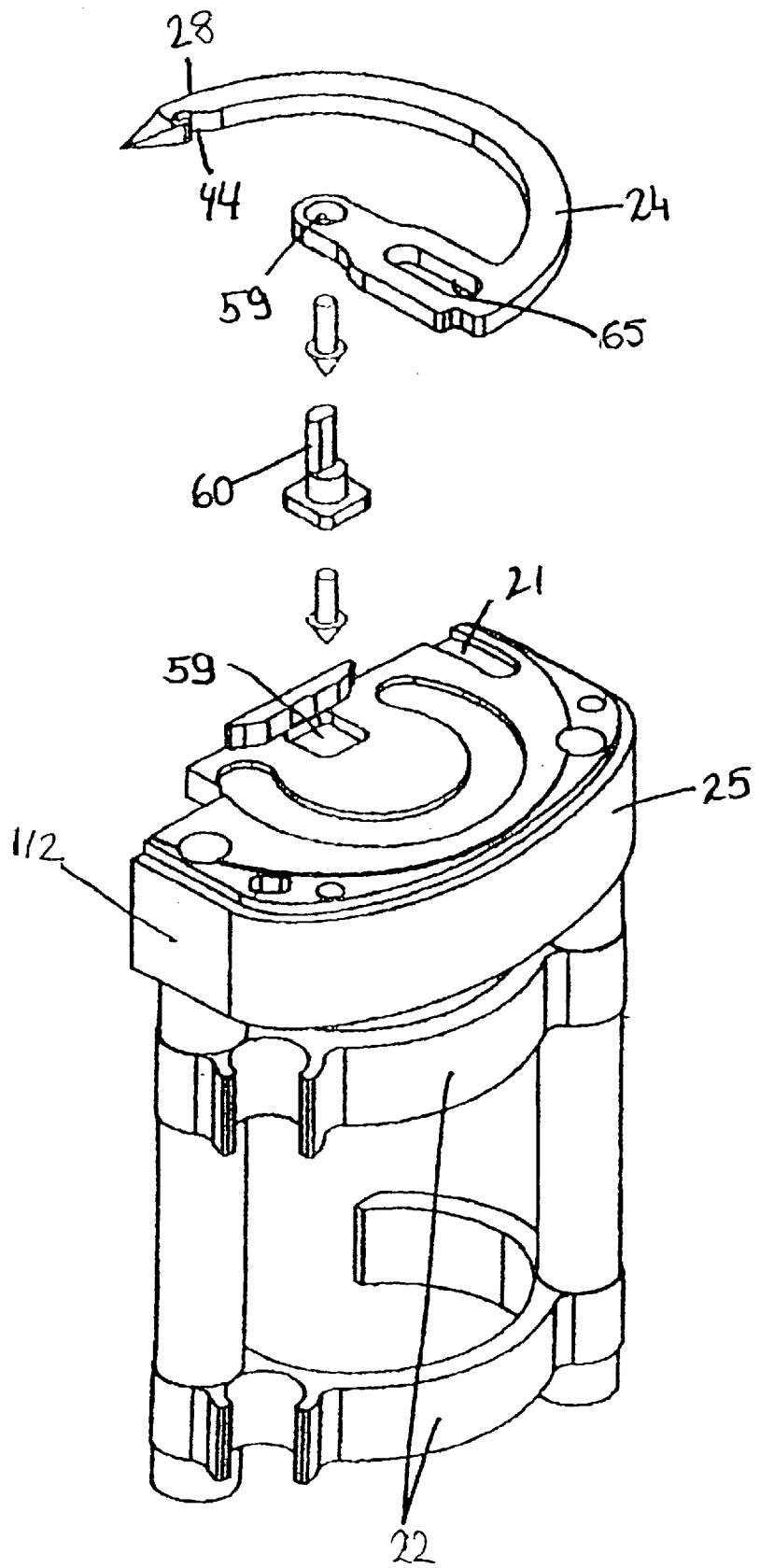
FIG. 11 is perspective view of the finger-guided suture device according to the embodiment depicted in FIG. 2 in which the assembly of the surgical needle is shown.
Figure 17:
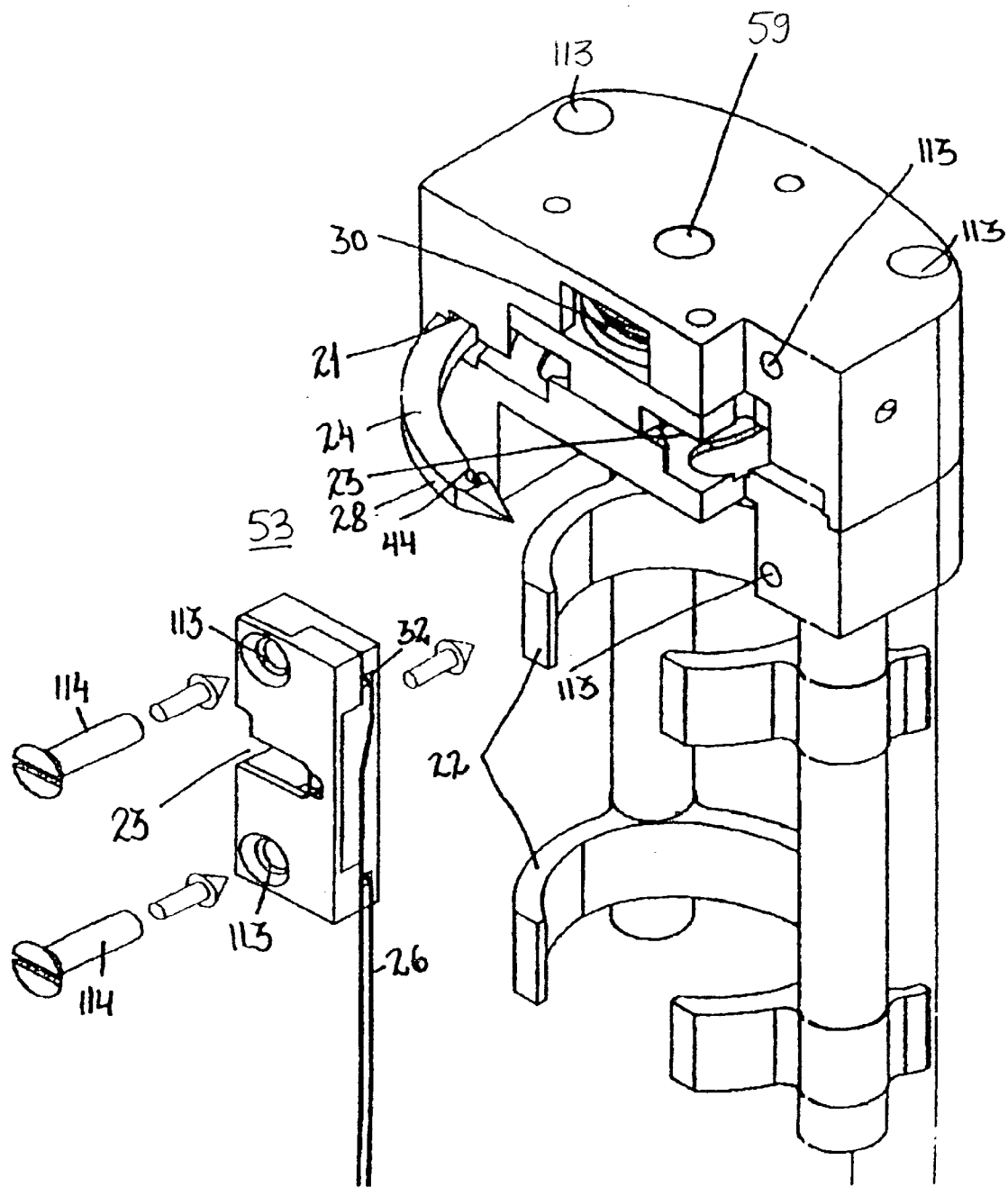
FIG. 17 depicts the assembly of the cartridge of the type depicted in FIG. 16 into the finger-guided suture device according to the embodiment depicted in FIG. 2.
Figure 18:
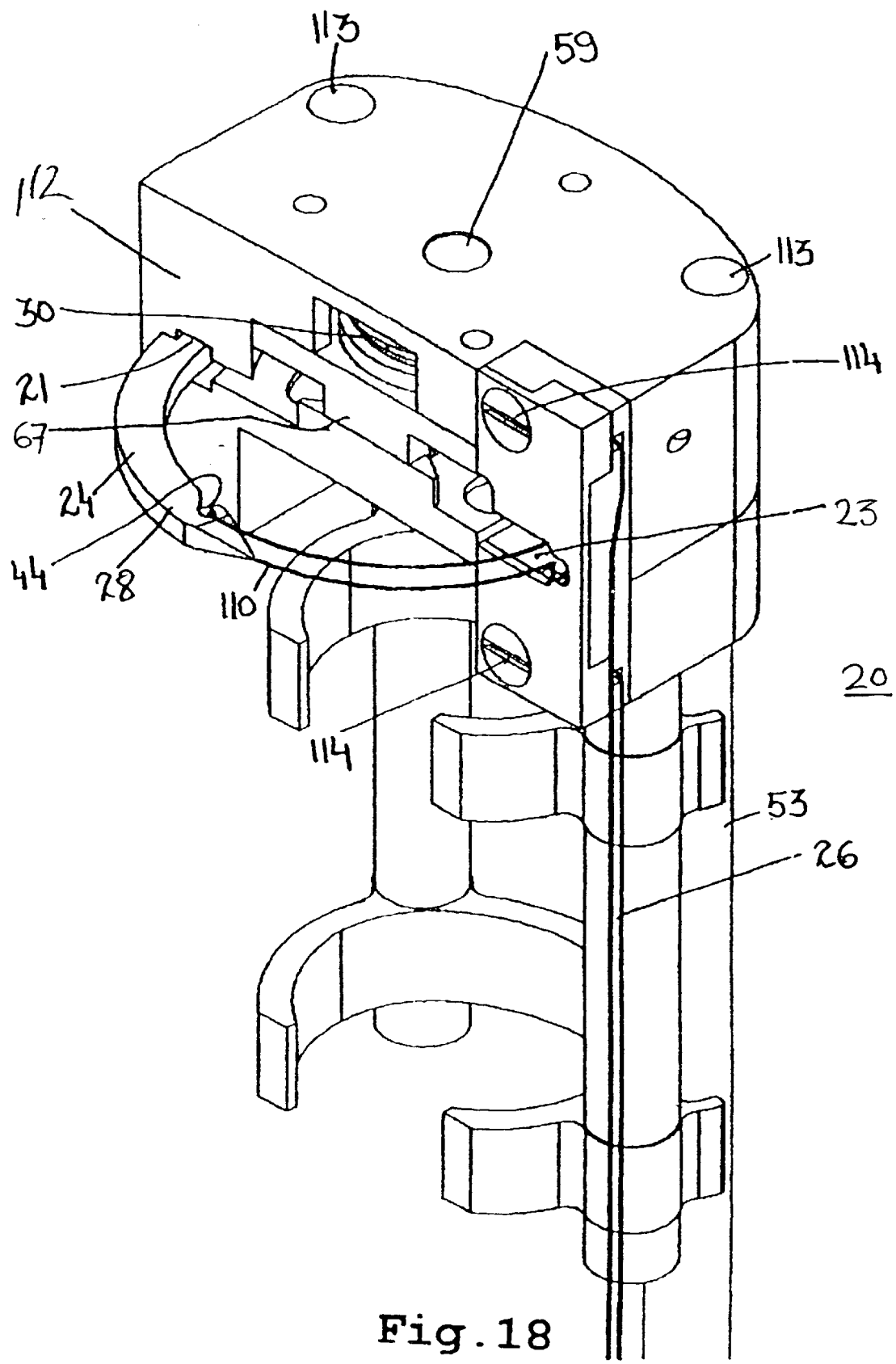
FIG. 18 is a perspective view of the finger-guided suture device according to the embodiment depicted in FIG. 2 in which engagement of the suture by the needle is depicted.
Figure 19:
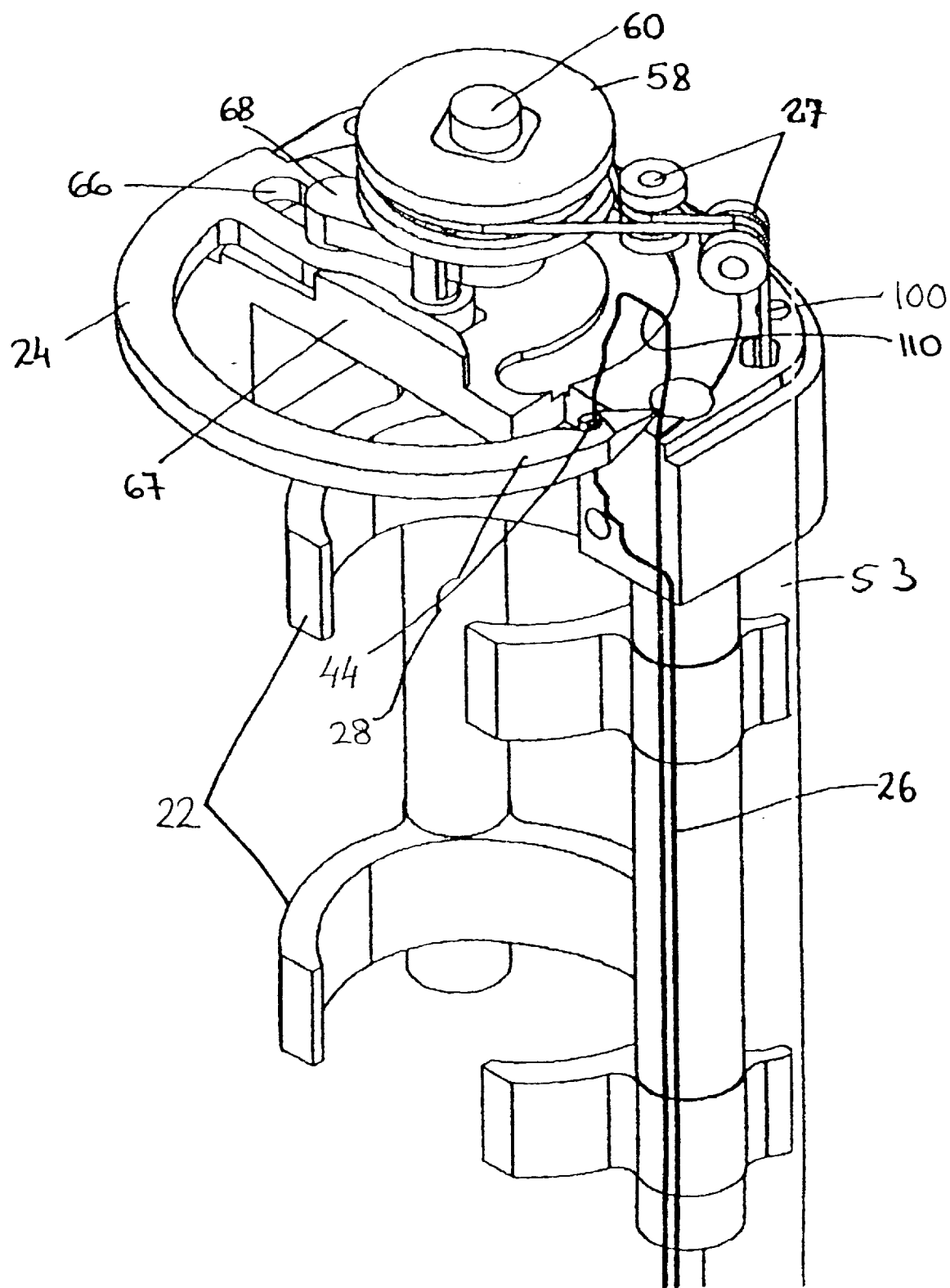
FIG. 19 is a cutaway view of the finger-guided suture device according to the embodiment depicted in FIG. 2 in which engagement of the suture by the needle is depicted.
Figure 20:
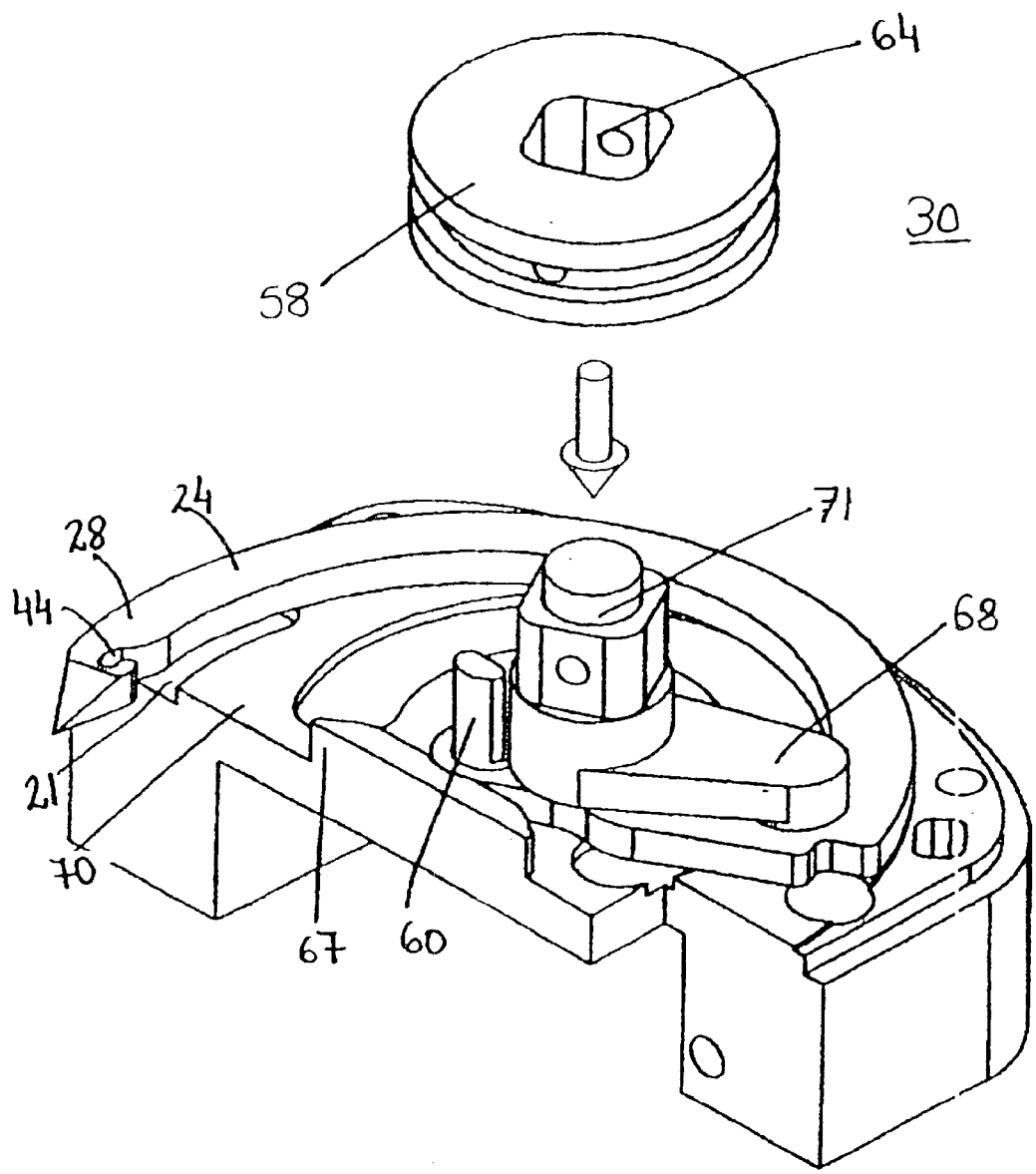
FIG. 20 is an exploded view of a portion of the finger-guided suture device according to the embodiment depicted in FIG. 2 in which the relative placements of the drive arm, needle and drive wheel are illustrated.
Figure 21:
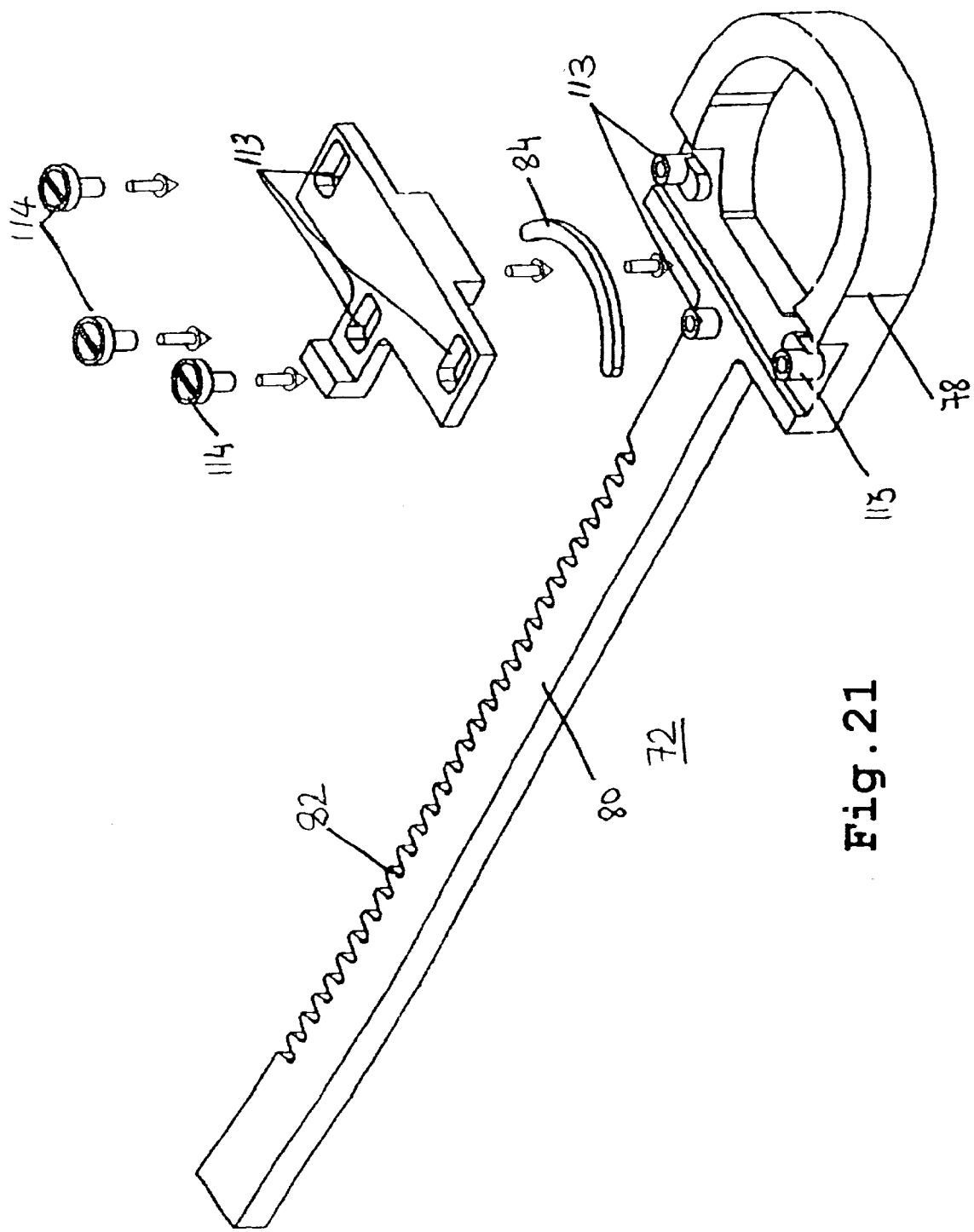
FIG. 21 is a perspective view of a handle of one embodiment of an external actuation device according to the present invention as pictured in FIGS. 1 and 2.
Figure 22:
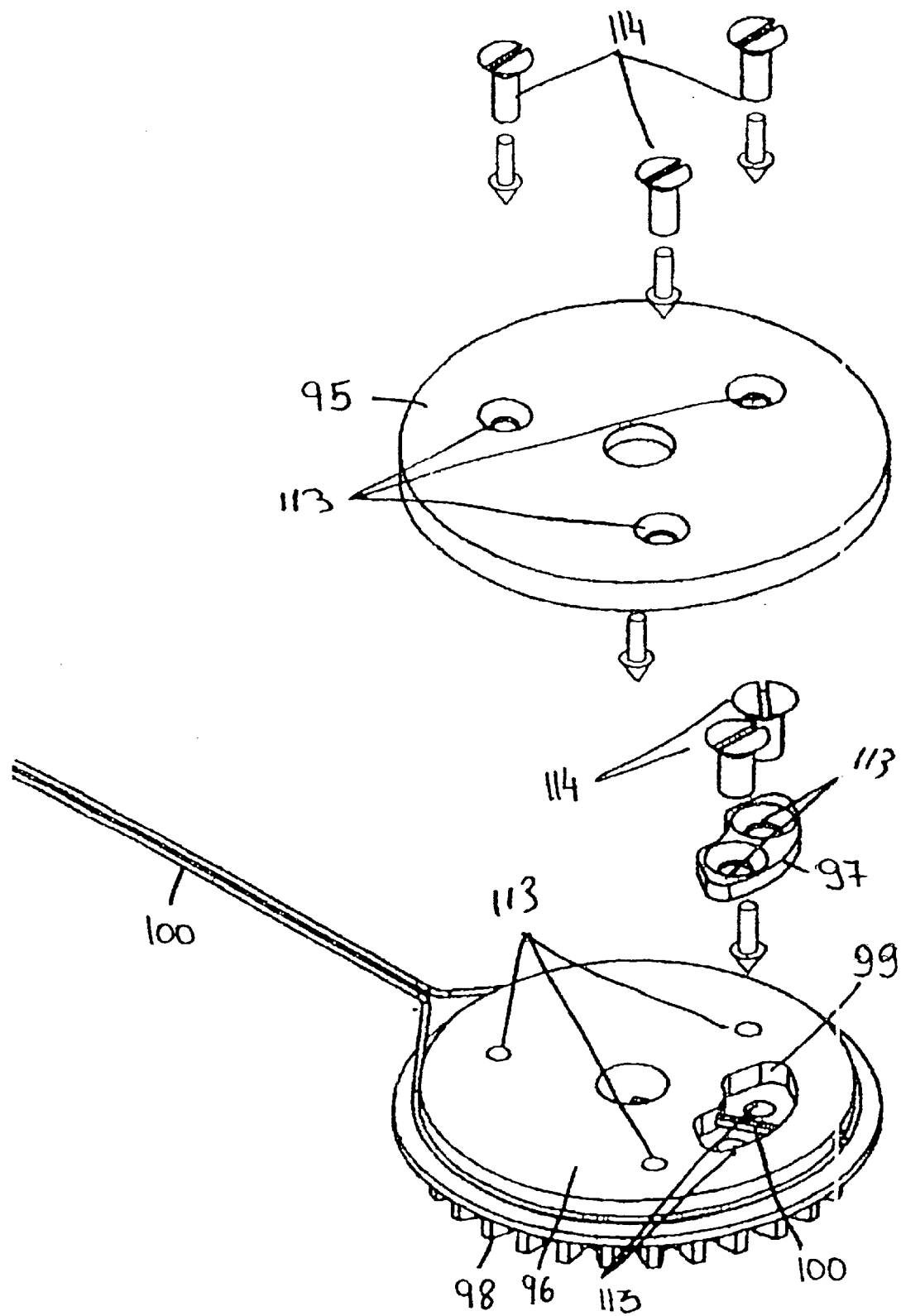
FIG. 22 is an exploded view of a portion of the drive mechanism of one embodiment of an external actuation device according to the present invention as pictured in FIGS. 1 and 2.

Thus, in the pictured preferred embodiments finger-guided suture device 20 further include surgical suture 26 formed with loop 110 (FIGS. 5 and 16) for collection by surgical needle 24. Loop 110 is contained within a cartridge 32 which serves for holding surgical suture 26 and for presenting it for collection via notch 44 formed at distal portion 28 of surgical needle 24. Cartridge 32 (FIGS. 5 and 16) includes at least one mechanism designed and constructed, so as to maintain a predetermined tension of surgical suture 26. A mechanism which is suitable for maintaining such a predetermined tension may be, for example, at least one piece of flexible material 36 containing at least one hole 38 through which surgical suture 26 passes. A single piece of flexible material 36 containing two holes 38 (FIG. 5) or a pair of pieces of flexible material 36 each containing one hole 38 (FIG. 16) can, for example, be employed. Flexible material 36 may be, for example, silicon, latex, rubber, fabric, or fabric with an eyelet. An eyelet may be constructed of material including, but not limited to, silicon, latex, rubber or fabric. Friction on suture 26 as it passes through cartridge 32 is reduced by rounding of corners 35 within cartridge 32. Cartridge 32 is covered with a cover 29 and affixed to housing 25 of device 20 by bolts 114 which pass through bolt holes 113 (FIGS. 6 and 17). Although bolts are pictured in all figures, other connecting means, including but not limited to, screws, rivets, nails, pins, glue, soldering, heat pressing and/or welding might be employed to assemble components of device 20 without substantially affecting its functions.

Drive mechanism 30 which serves for driving needle 24 includes a first portion 54 (FIGS. 3, 7, 12 and 14) engaged within housing 25. First portion 54 is in contact with needle 24. Drive mechanism 30 also includes a second, remote, portion 56 (FIGS. 1 and 2) extending out of the patient's body and which is operable by a free hand of the surgeon so as to eject needle 24 from thimble-like element 22. Pipe or tube 53 containing cable 100 operatively connects first portion 54 to second portion 56.

Figure 3:
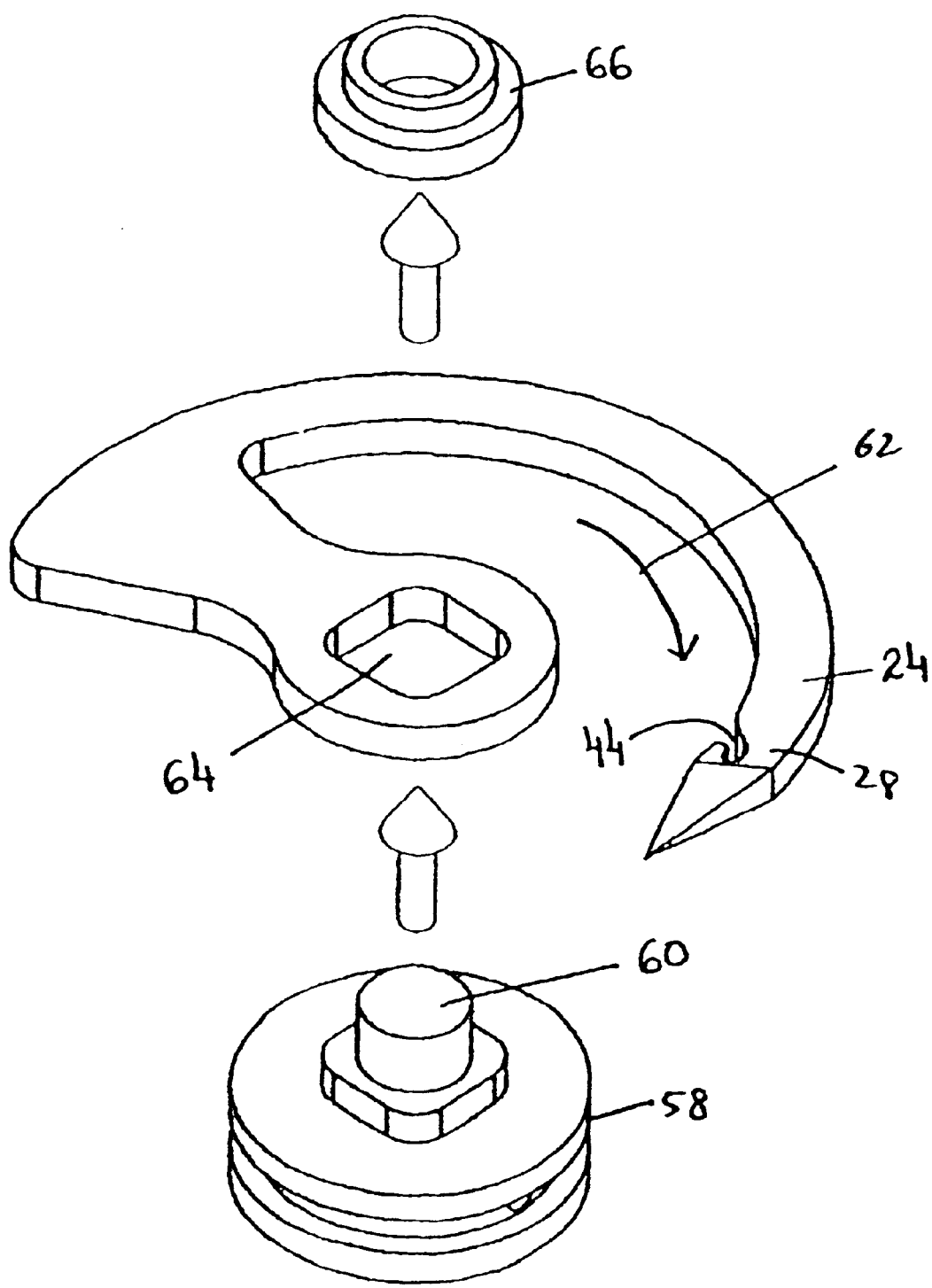
FIG. 3 depicts the assembly of a surgical needle and a drive wheel according to the embodiment of the finger-guided suture device depicted in FIG. 1.
Figure 4:
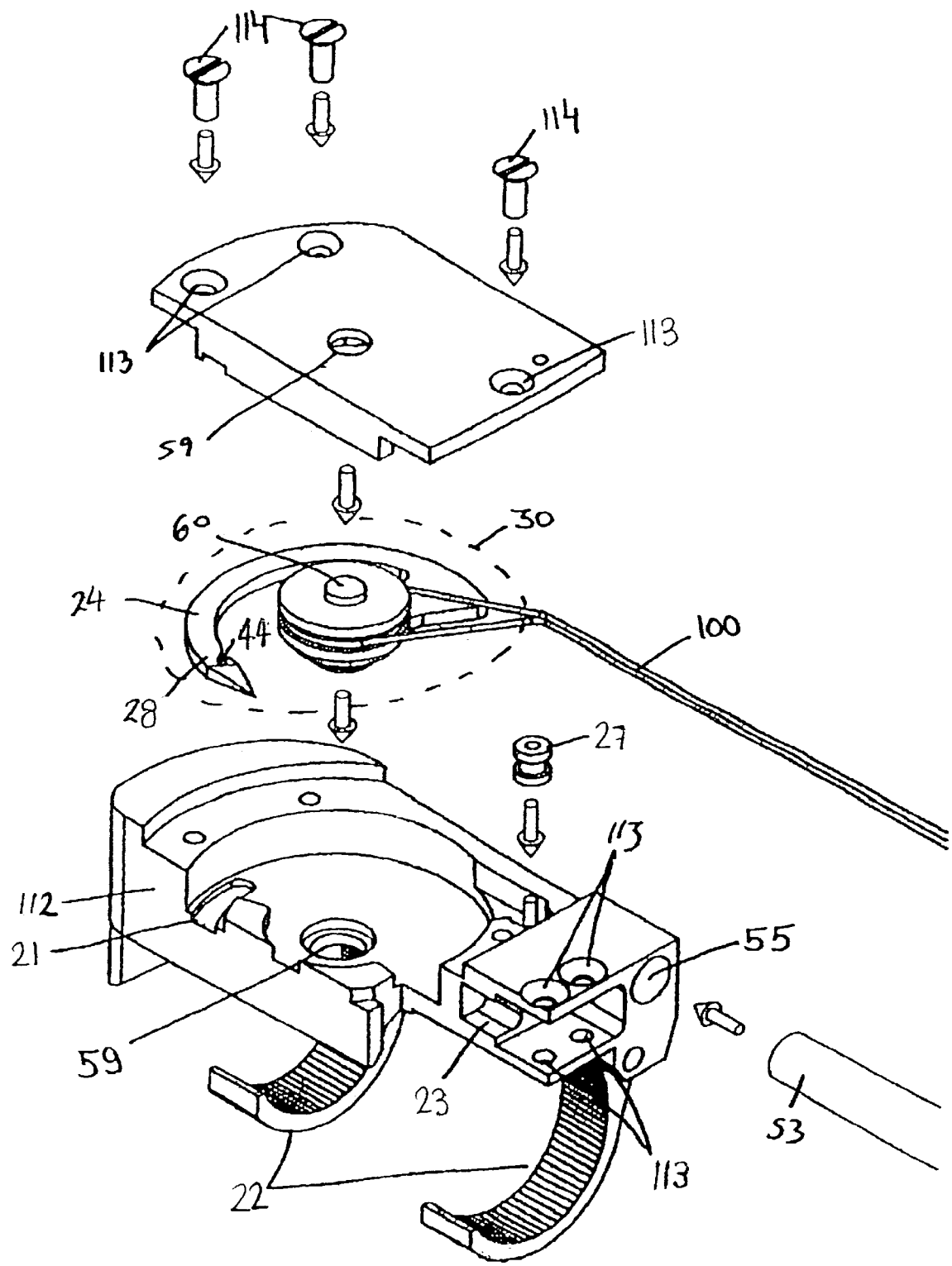
FIG. 4 is an exploded view of the finger-guided suture device according to the embodiment depicted in FIG. 1.
Figure 5:
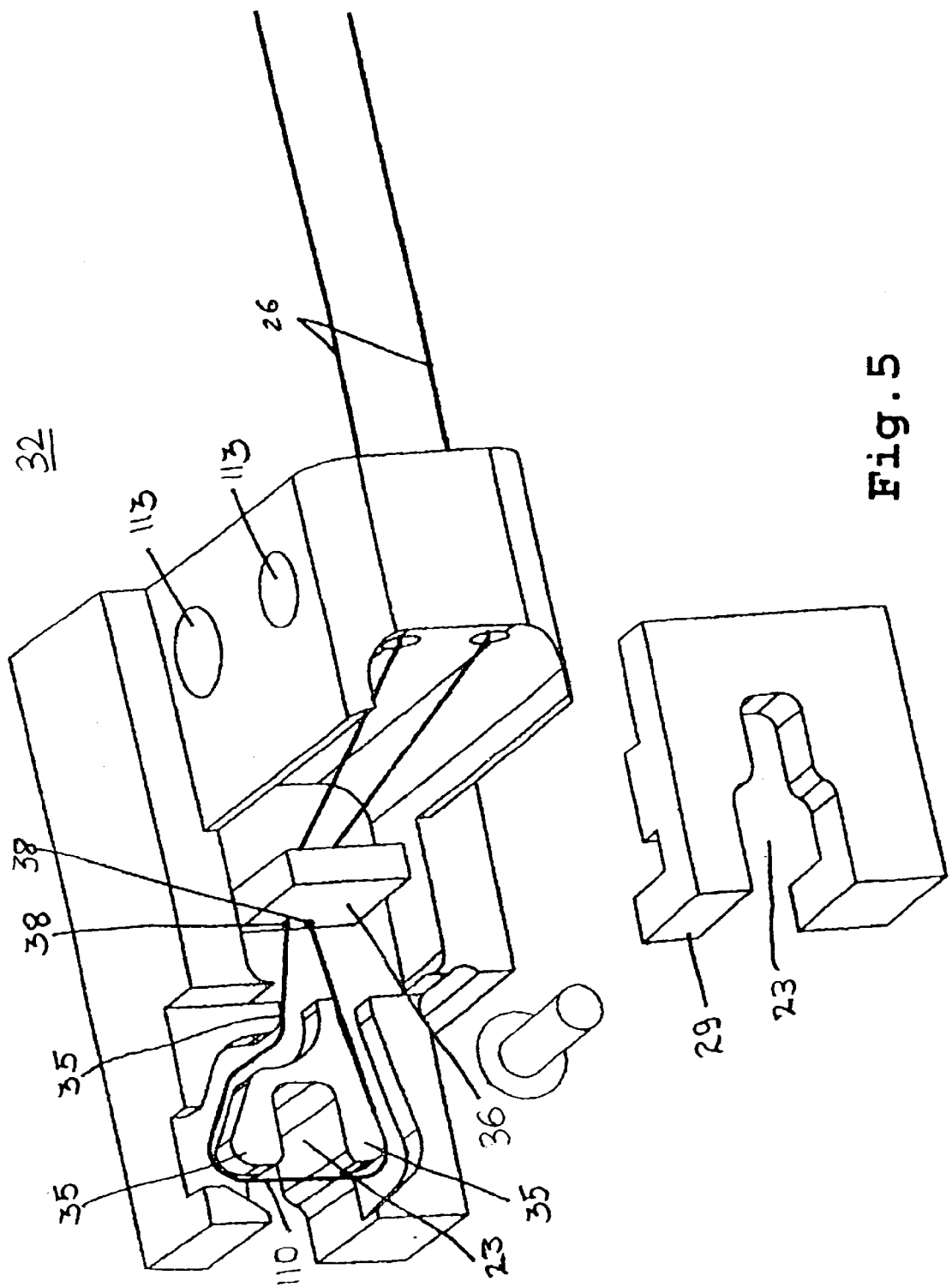
FIG. 5 depicts a cartridge, with cover removed, of the finger-guided suture device according to the embodiment depicted in FIG. 1.

According to one pictured preferred embodiment (FIGS. 3 and 7) first portion 54 of mechanism 30 includes a rotatable wheel 58 having an axle 60. Axle 60 serves for engaging surgical needle 24 and imparting thereto a rotational motion 62 in at least one direction. Axle 60 fits into axle seats 59 (FIG. 4). Cable 100 is contained in pipe 53 which is seated in pipe seat 55. Pulley 27 serves to reduce friction on cable 100. According to this preferred embodiment, needle 24 includes a mechanism 64 for engaging rotatable wheel 58. Further according to this preferred embodiment, first portion 54 of mechanism 30 also includes a locking piece 66 for insuring that surgical needle 24 and rotatable wheel 58 remain engaged.

Figure 12:
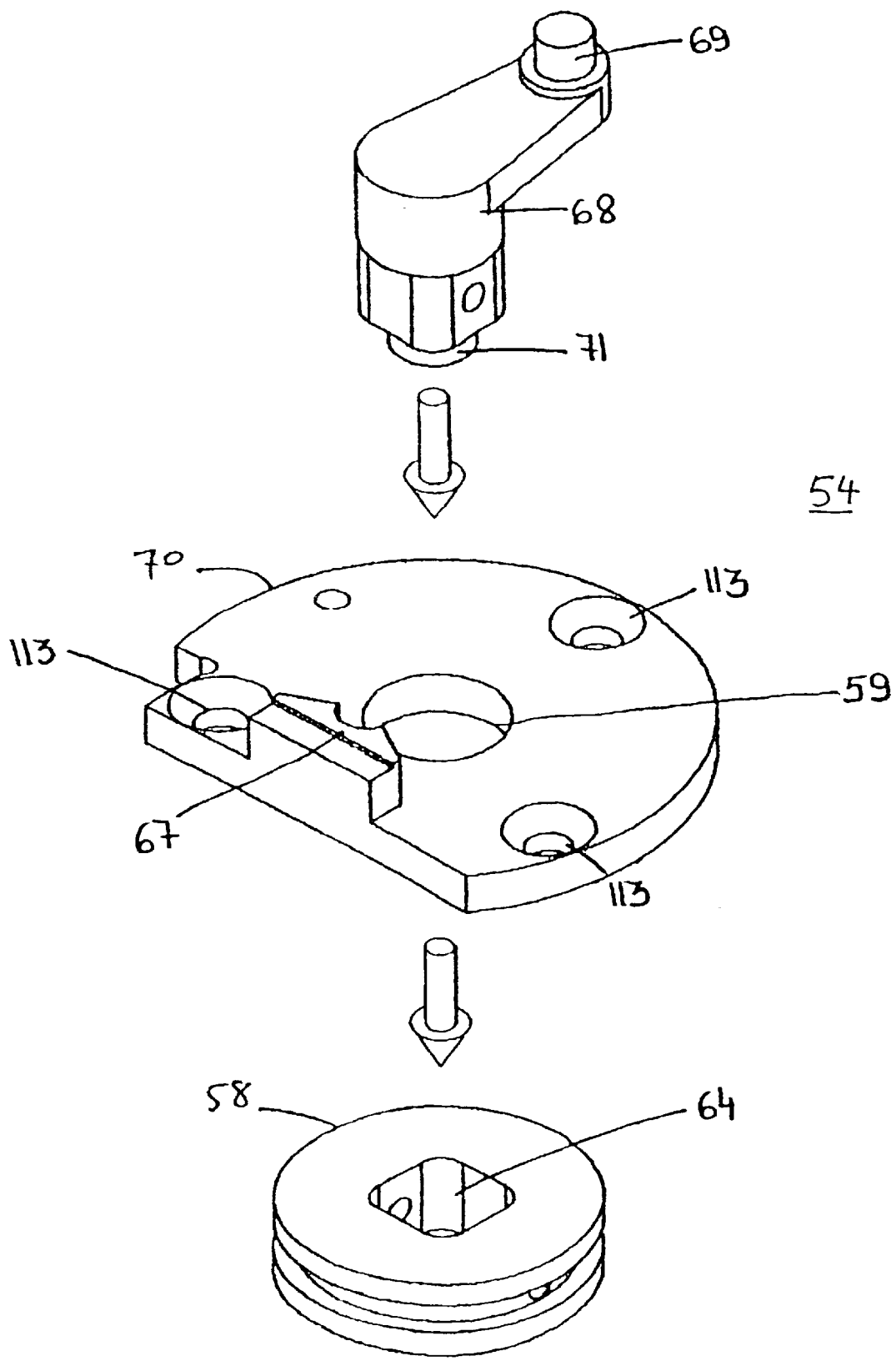
FIG. 12 is a an exploded view of a drive arm of the finger-guided suture device according to the embodiment depicted in FIG. 2.
Figure 13:
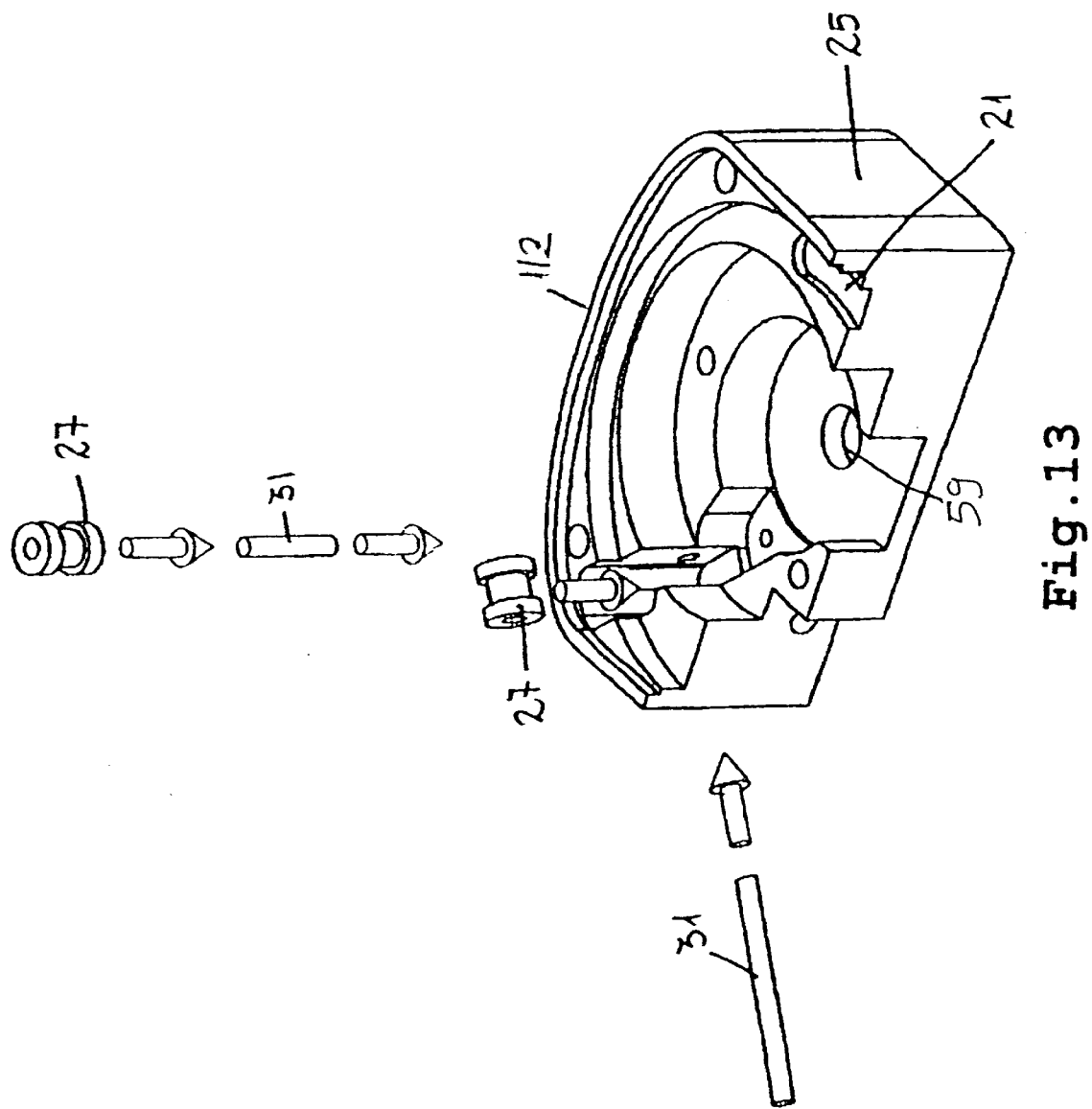
FIG. 13 is an exploded view detailing assembly of pulleys of a finger-guided suture device according to the embodiment depicted in FIG. 2.
Figure 14:
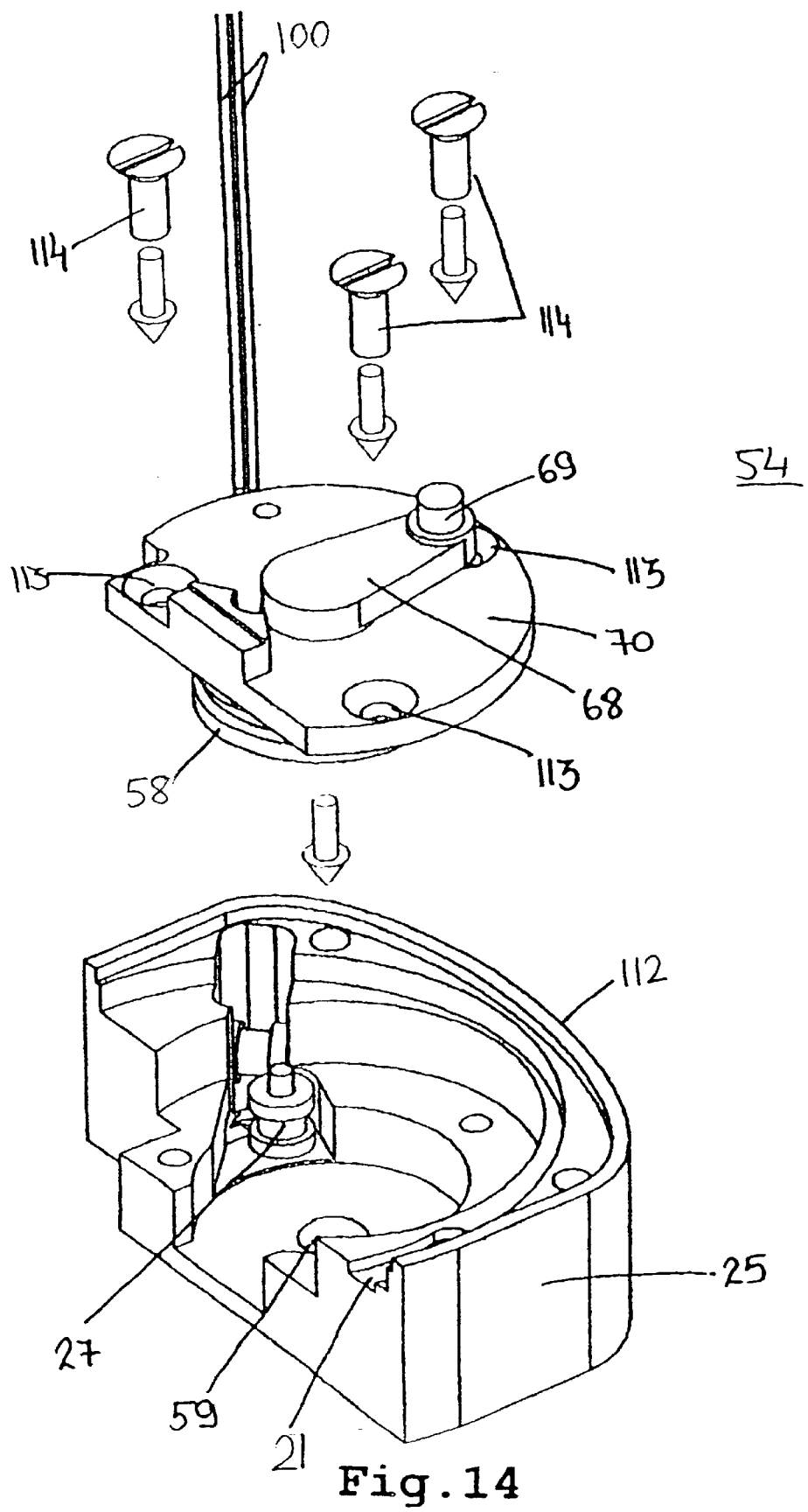
FIG. 14 is an exploded view of a finger-guided suture device according to the embodiment depicted in FIG. 2 showing assembly of the drive arm and drive wheel.
Figure 15:
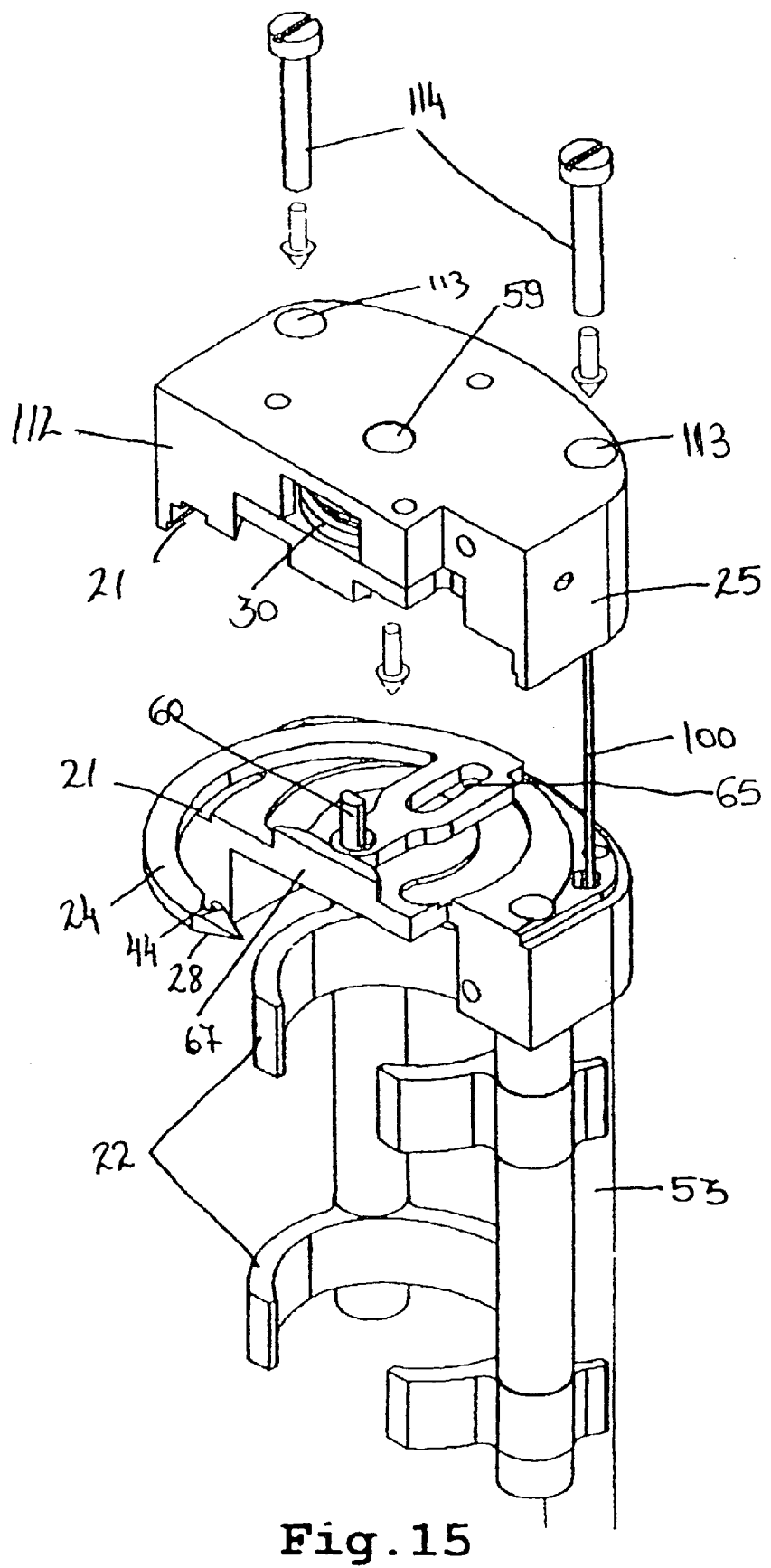
FIG. 15 depicts the assembly of the upper and lower portions of the finger-guided suture device according to the embodiment depicted in FIG. 2.
Figure 16:
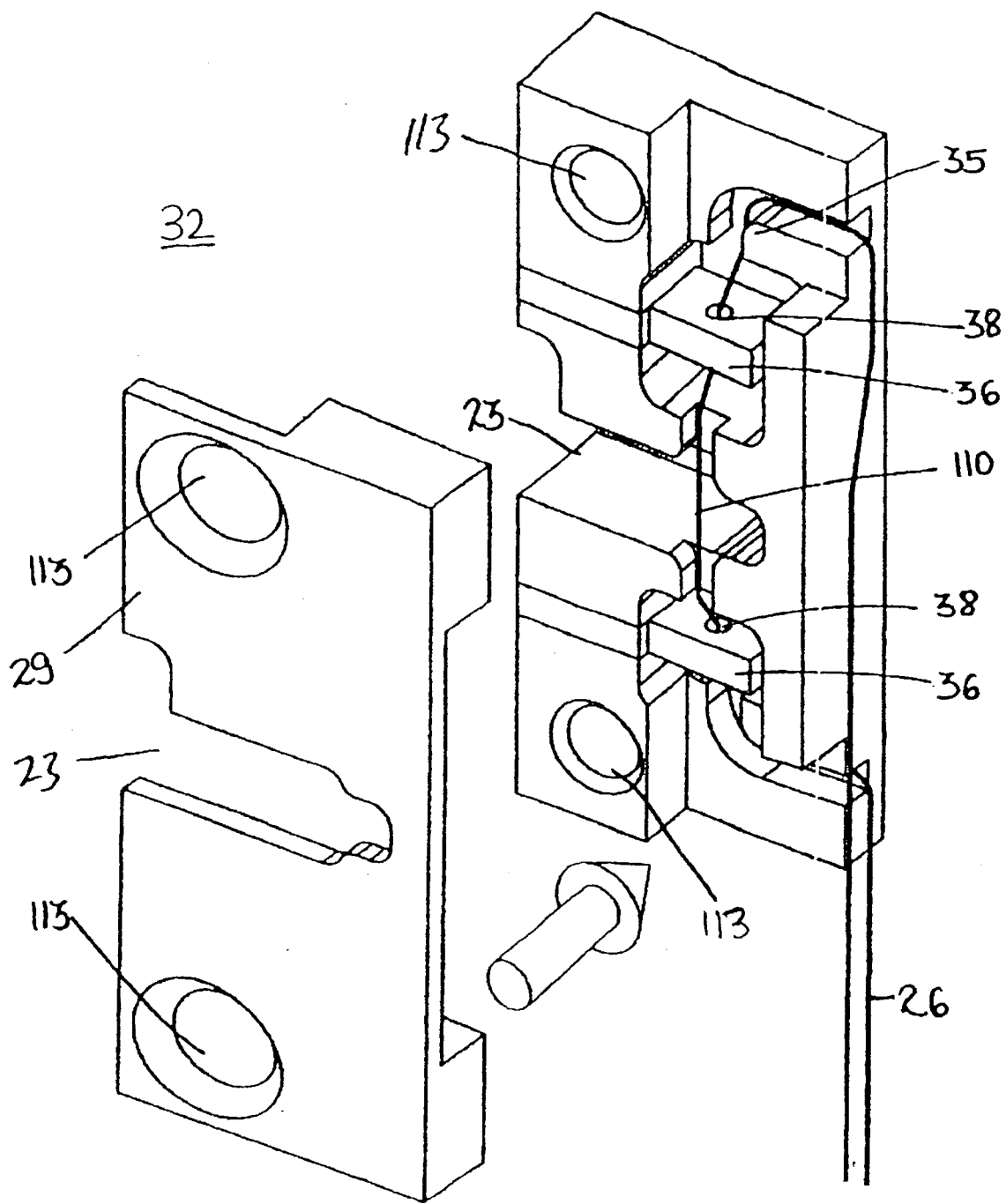
FIG. 16 is an exploded view of a cartridge of the finger-guided suture device according to the embodiment depicted in FIG. 2.

According to an alternative pictured preferred embodiment (FIGS. 12 and 14) first portion 54 of mechanism 30 includes rotatable wheel 58 which has mechanism 64 which serves for engaging an axle 71 of a drive arm 68 and imparting a rotational motion, as indicated by 62, in at least one direction thereto. Drive arm 68 is designed and constructed to be engageable by both rotatable wheel 58 and needle 24. A needle engaging piece 69 fits into a mechanism 65 which serves for engaging drive arm 68 of needle 24 and imparts a rotational motion, as indicated at 62, of rotatable wheel 58 in at least one direction to surgical needle 24. A disk 70 ensures that needle 24, drive arm 68 and rotatable wheel 58 remain engaged. In this preferred embodiment cable 100 passes over a pair of pulleys 27 mounted on a pair of axles 31 in housing 25 (FIG. 13). Needle 24 rotates about axle 60 (FIG. 11) and has a range of motion which is restricted by a stopping piece 67 (FIG. 12). Again, pipe 53 serves to contain cable 100.

Remote portion 56 (FIGS. 21–30) of drive mechanism 30 includes a hand operable actuator 72 (FIG. 21) for operating drive mechanism 30. Remote portion 56 also includes a drive housing 76 for containing at least a portion 74 of drive mechanism 30, and at least a portion 74 (FIG. 22) of drive mechanism 30. Drive mechanism 30 functions to impart a rotational motion in at least one direction to needle 24.

Hand operable actuator 72 of remote portion 56 of drive mechanism 30 includes a handle 78 for engaging at least one finger of the free hand of the surgeon. Actuator 72 of remote portion 56 also includes an extending piece 80 containing a plurality of arcuate teeth 82. Extending piece 80 is movable through drive housing 76 by means of pressure applied to handle 78 by at least one finger of the free hand of the surgeon. Actuator 72 of remote portion 56 also includes a pressure sensitive spring 84 and a brake handle 86. Brake handle 86 is operable in a first direction by pressure sensitive spring 84 and in a second direction by the at least one finger of the free hand of the surgeon.

Figure 23:
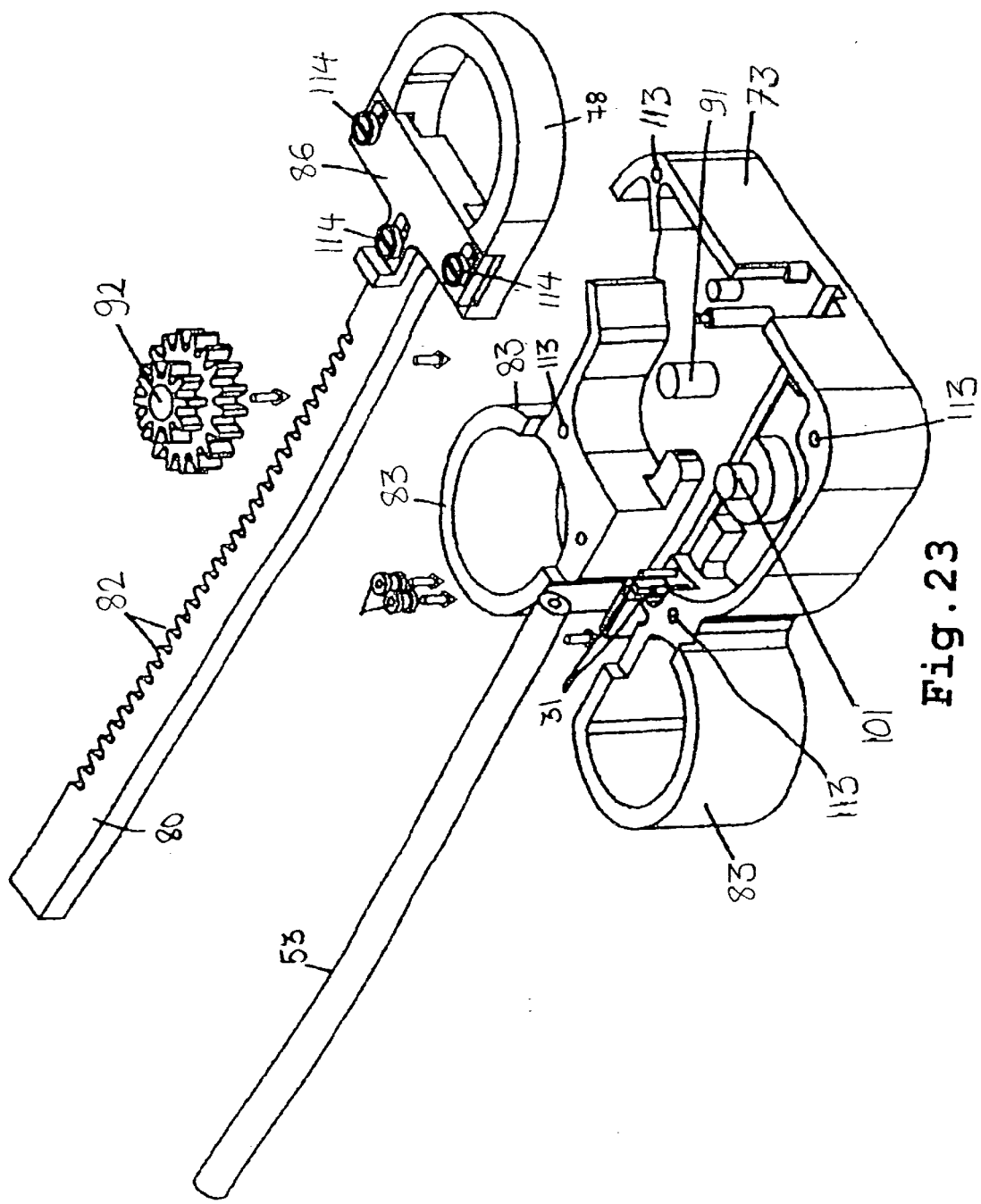
FIG. 23 is an exploded view of the drive housing of the drive mechanism of one embodiment of an external actuation device according to the present invention as pictured in FIGS. 1 and 2, showing the assembly of a handle and a first drive wheel therein.
Figure 24:
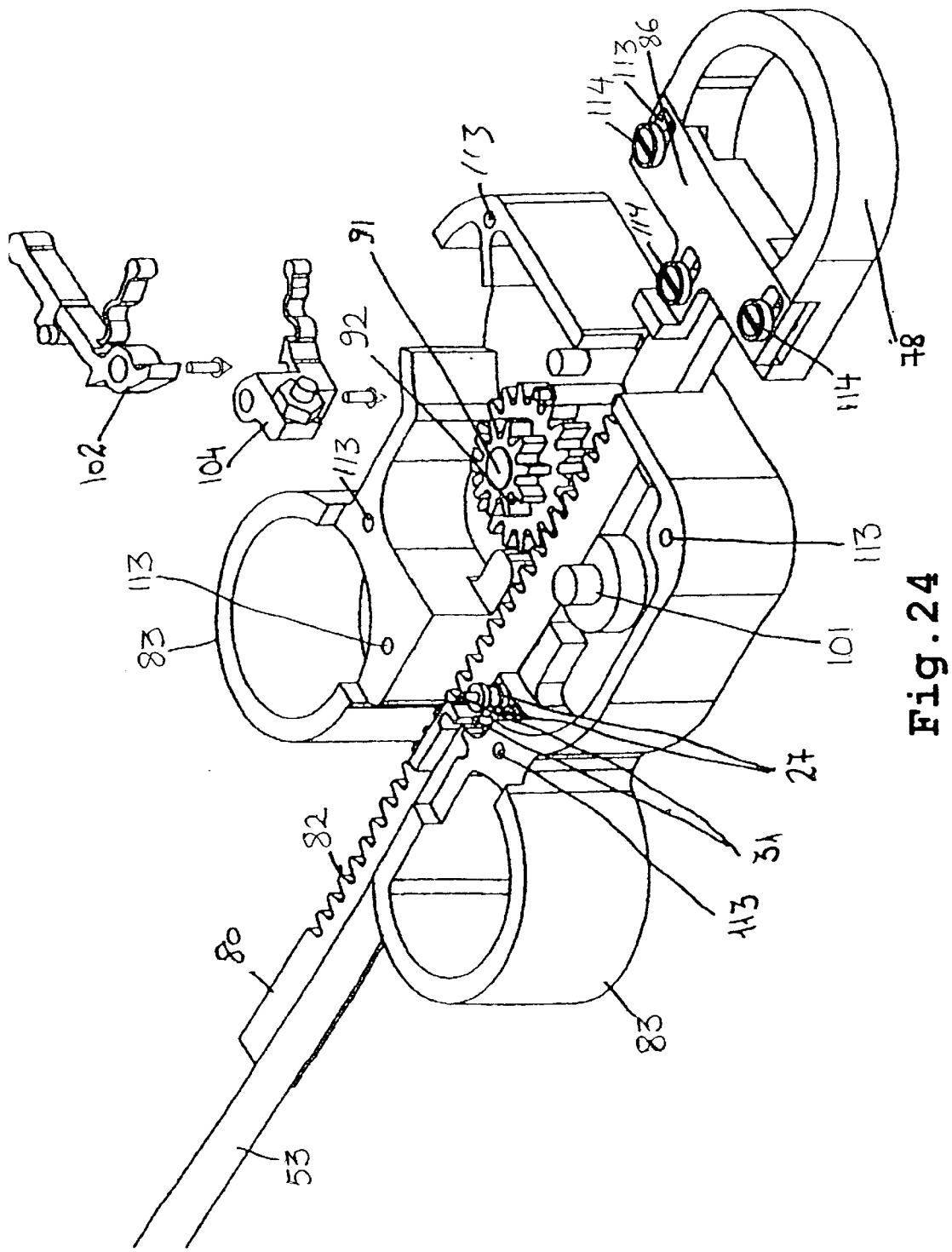
FIG. 24 is an exploded view of the drive housing of the drive mechanism of one embodiment of an external actuation device according to the present invention as pictured in FIGS. I and 2, showing the assembly of a lockable ratchet and a ratchet locking arm therein.
Figure 25:
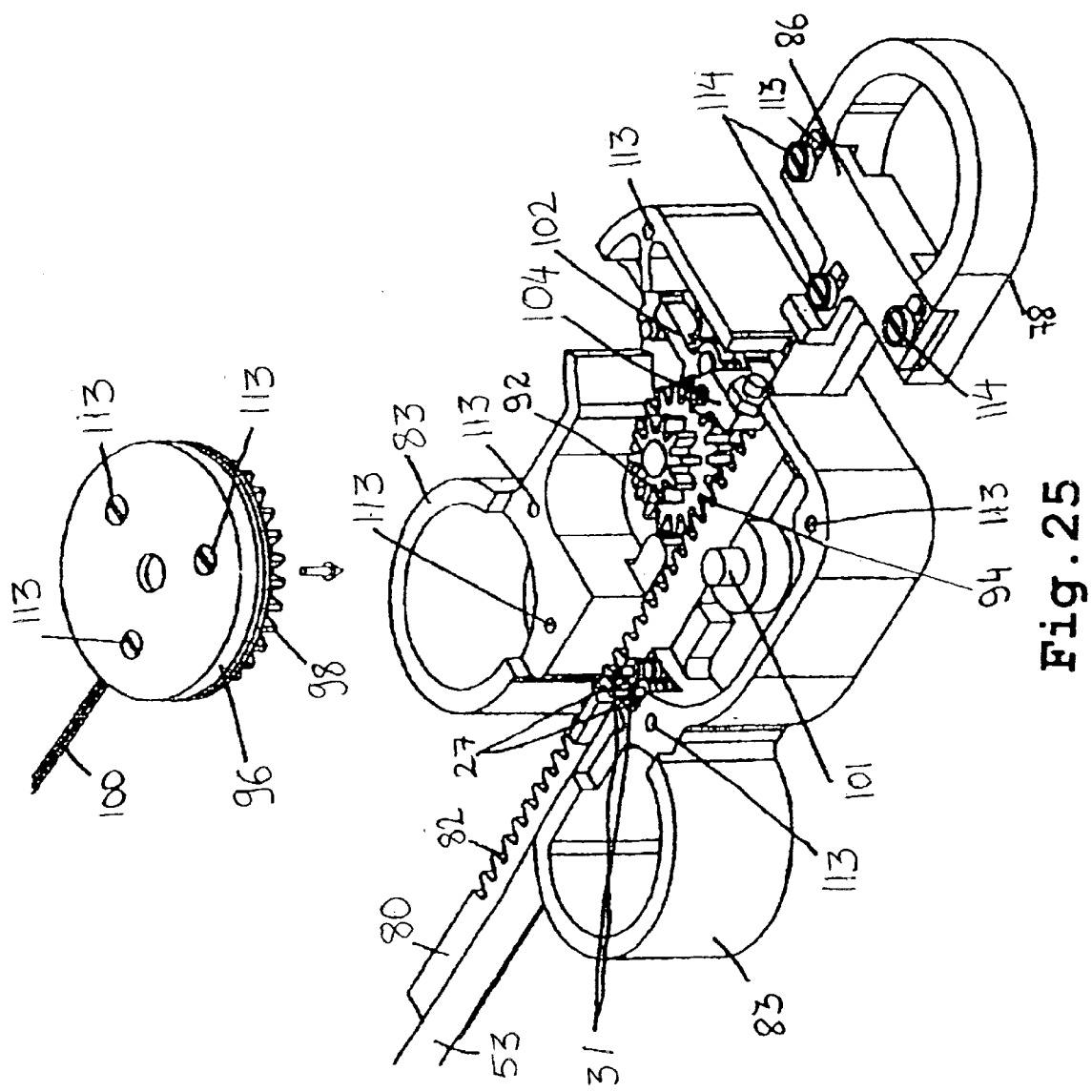
FIG. 25 depicts the assembly of the portion of the drive mechanism shown in FIG. 22 into the drive housing of FIGS. 23 and 24.
Figure 26:
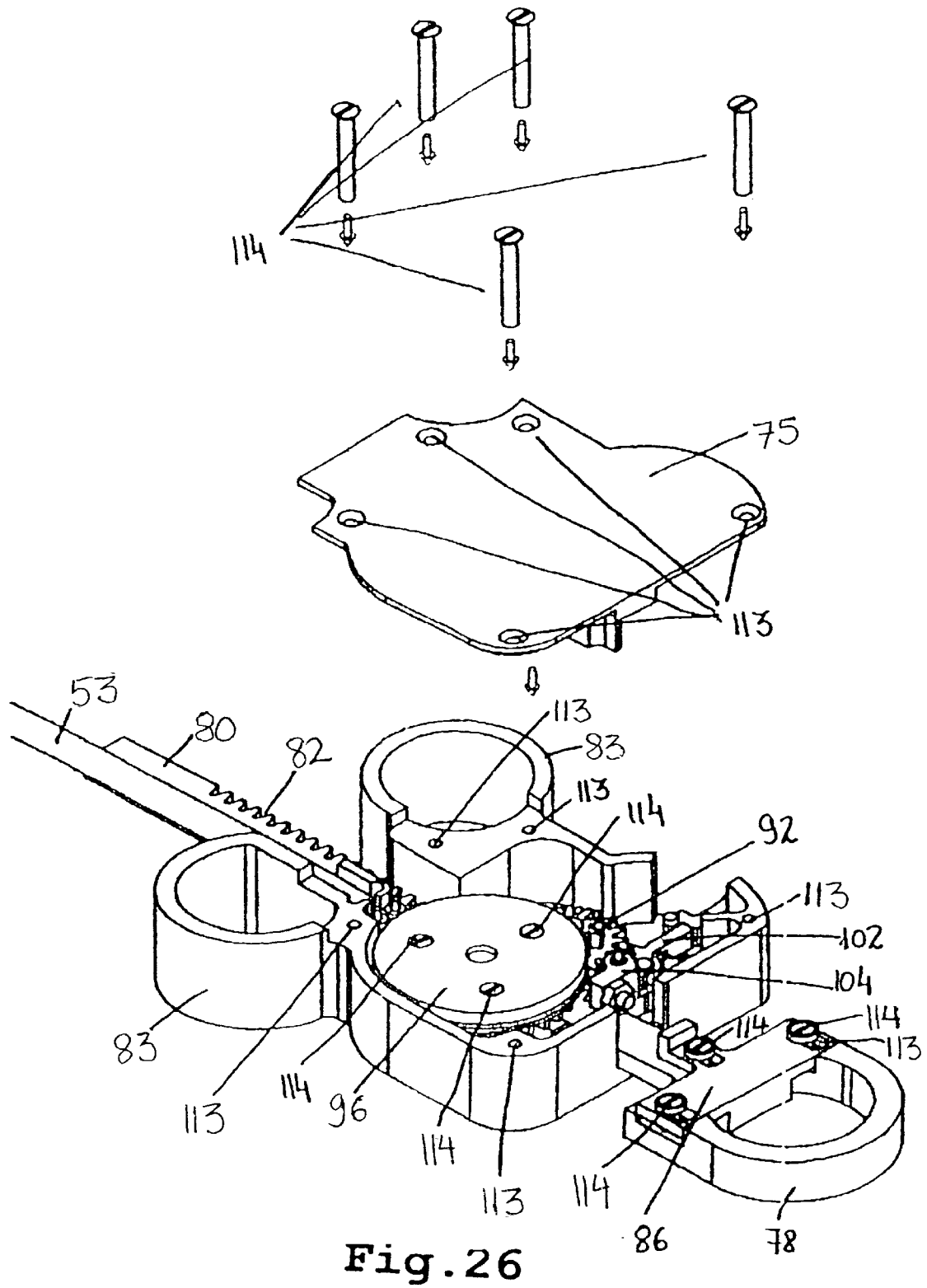
FIG. 26 depicts positioning of a cover on the drive housing of FIGS. 23 and 24 and 25.
Figure 27:
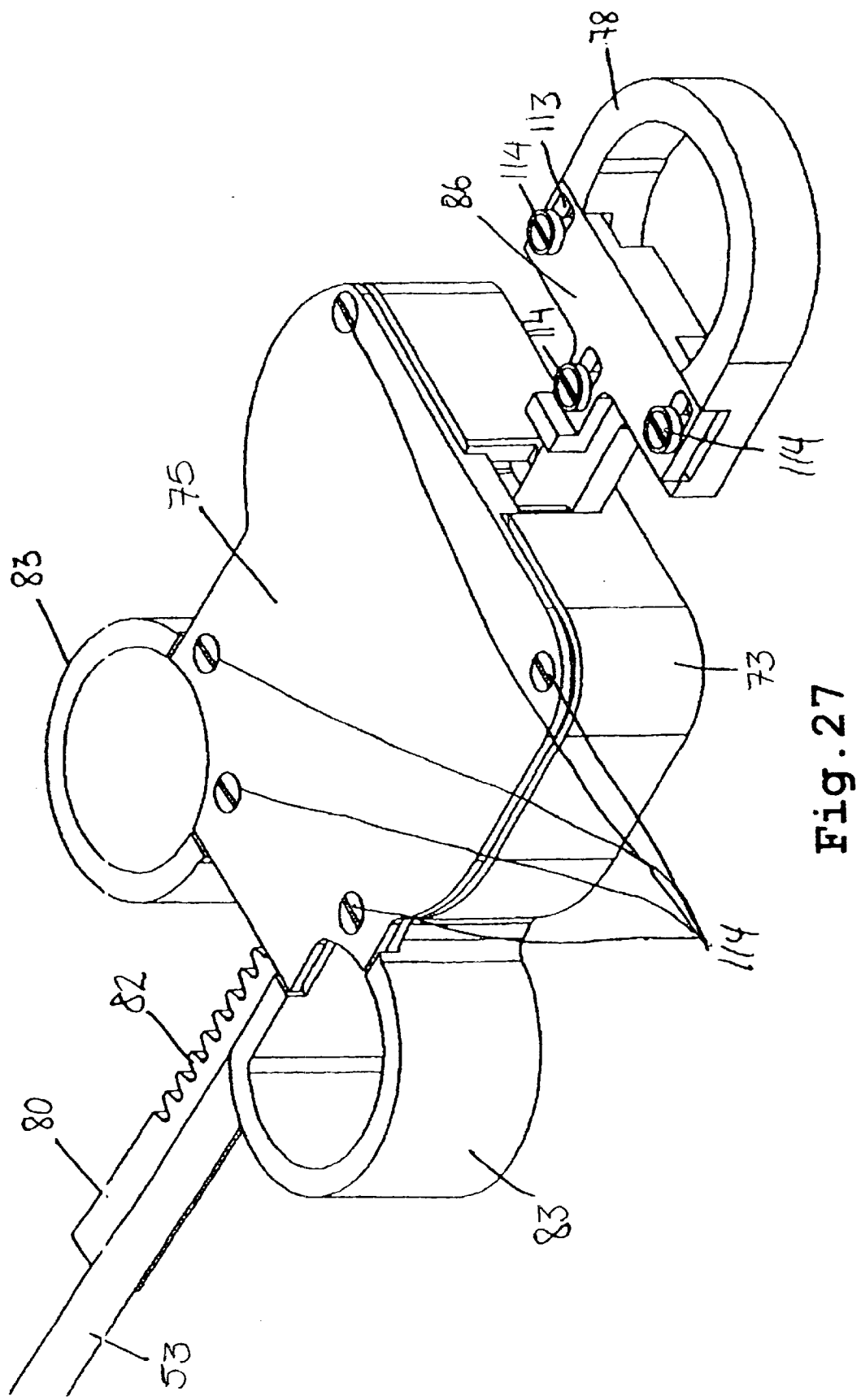
FIG. 27 shows the covered drive housing of FIG. 26 with the handle of FIG. 21 protruding.

Remote portion 56 of drive mechanism 30 includes plurality of arcuate teeth 82 deployed in a linear arrangement along an extending piece 80 of handle 78. Drive mechanism 30 further includes a first gear 92 with a first circular arrangement of arcuate teeth 94. First circular arrangement of arcuate teeth 94 serves for engaging plurality of arcuate teeth 82 along extending piece 80. Linear displacement of extending piece 80 is therefore translated into rotational motion of first gear 92. Remote portion 56 of drive mechanism 30 further includes a second gear 96. Second gear 96 includes a second circular arrangement of arcuate teeth 98 for engaging first circular arrangement of arcuate teeth 94 of first gear 92. In the pictured embodiment, second circular arrangement of arcuate teeth 98 is actually two concentric circular arrangements of arcuate teeth, although a single circular arrangement of arcuate teeth might be employed without significantly affecting the performance of device 20. A cover 95 covers second gear 96. Cable 100 is fitted around at least a portion of second gear 96 and is fixed to gear 96 in at least one point by a cable holding piece 97, placed in a holding piece well 99 and secured via bolts 114 which fit into bolt holes 113. Therefore, rotational motion of first gear 92 causes rotational motion of second gear 96. Remote portion 56 of drive mechanism 30 further includes at least a portion of cable 100 in contact with at least one point on second gear 96, such that rotational motion of second gear 96 is translated to linear motion of cable 100. First gear 92 and second gear 96 are fitted on, and rotate about, axles 91 and 101, respectively (FIG. 23).

In the pictured preferred embodiments of device 20, remote portion 56 of drive mechanism 30 further includes a ratchet 102 for alternately engaging and releasing at least one arcuate tooth 94 of the first gear 92. Remote portion 56 of drive mechanism 30 further includes a ratchet control arm 104 for alternately engaging and releasing ratchet 102. Remote portion 56 of drive mechanism 30 further includes a brake handle 86 for alternately operating the ratchet control arm. These components are operatively arranged so that when brake handle 86 operates ratchet control arm 104, ratchet control arm 104 releases ratchet 102, ratchet 102 engages at least one arcuate tooth 94 of first gear 92 and preventing it from rotating. This means that when brake handle 86 does not operate ratchet control arm 104, ratchet control 104 arm engages ratchet 102, ratchet 102 releases at least one arcuate tooth 94 of first gear 92 which is then free to rotate.

Figure 28:
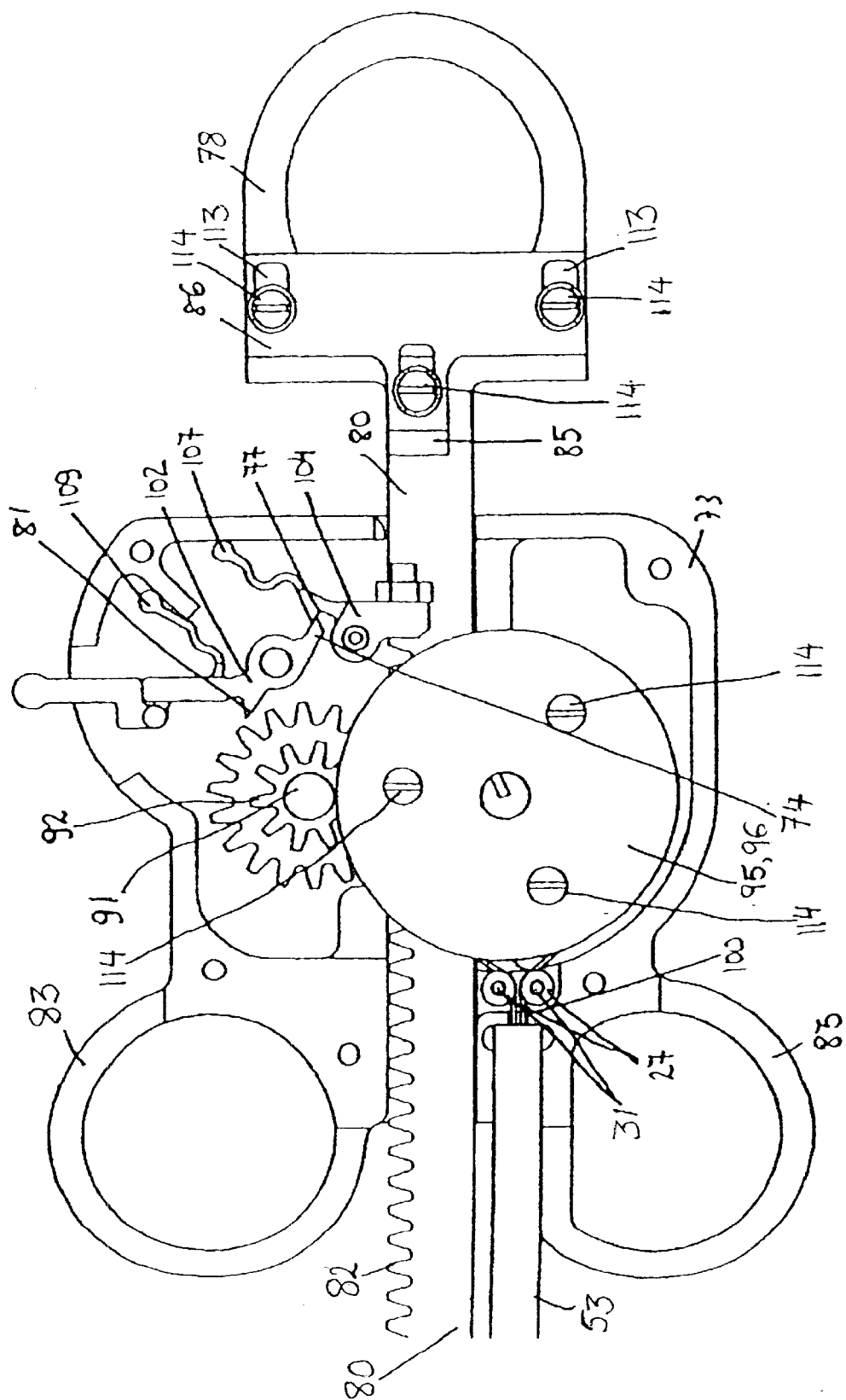
FIG. 28 is a cutaway top view of the assembled drive housing of FIGS. 25, 26 and 27 showing engagement of the ratchet locking arm with the locking ratchet.
Figure 29:
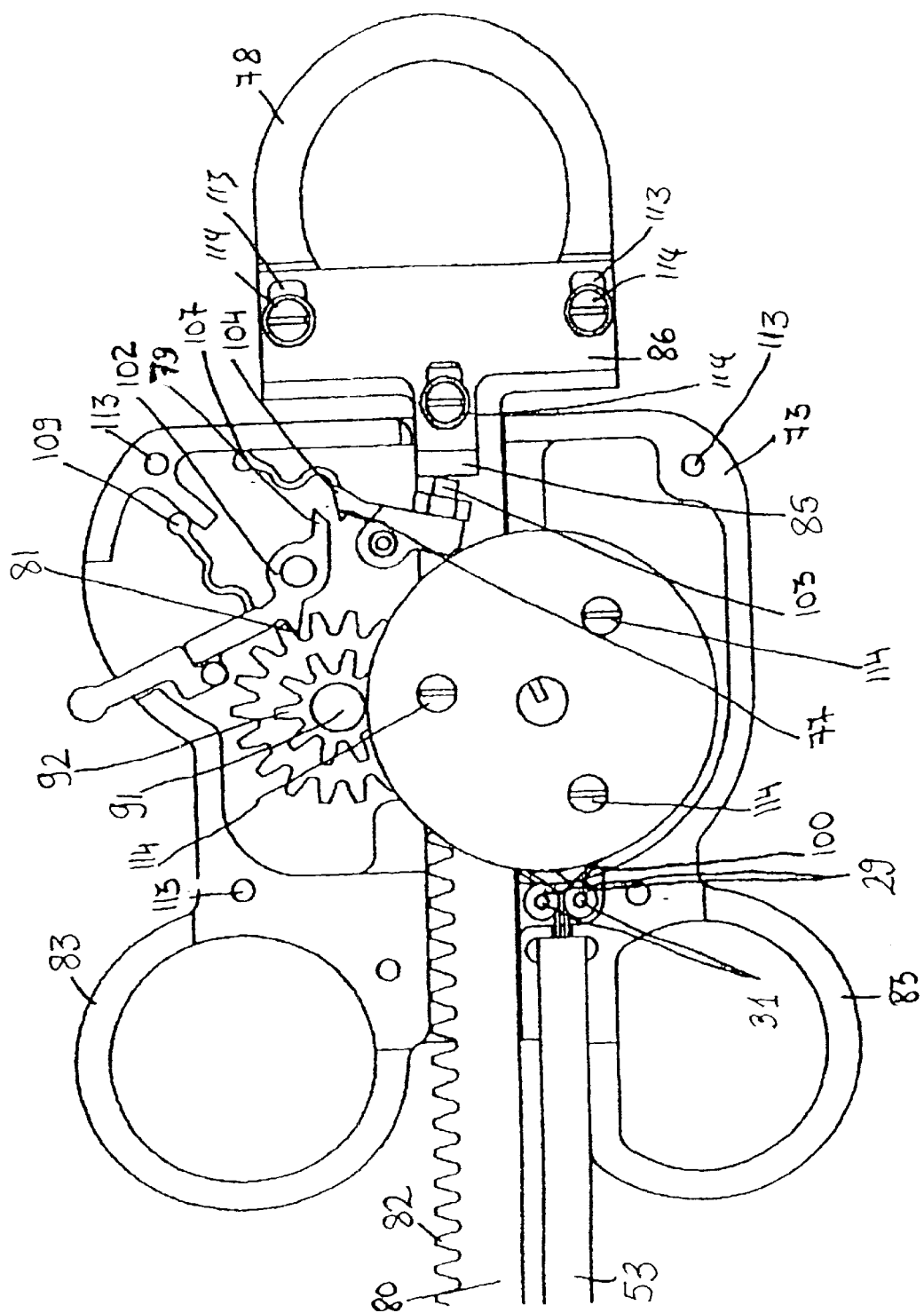
FIG. 29 is a cutaway top view of the assembled drive housing of FIGS. 25, 26 and 27 and 28 showing dis-engagement of the ratchet locking arm from the locking ratchet.
Figure 30:
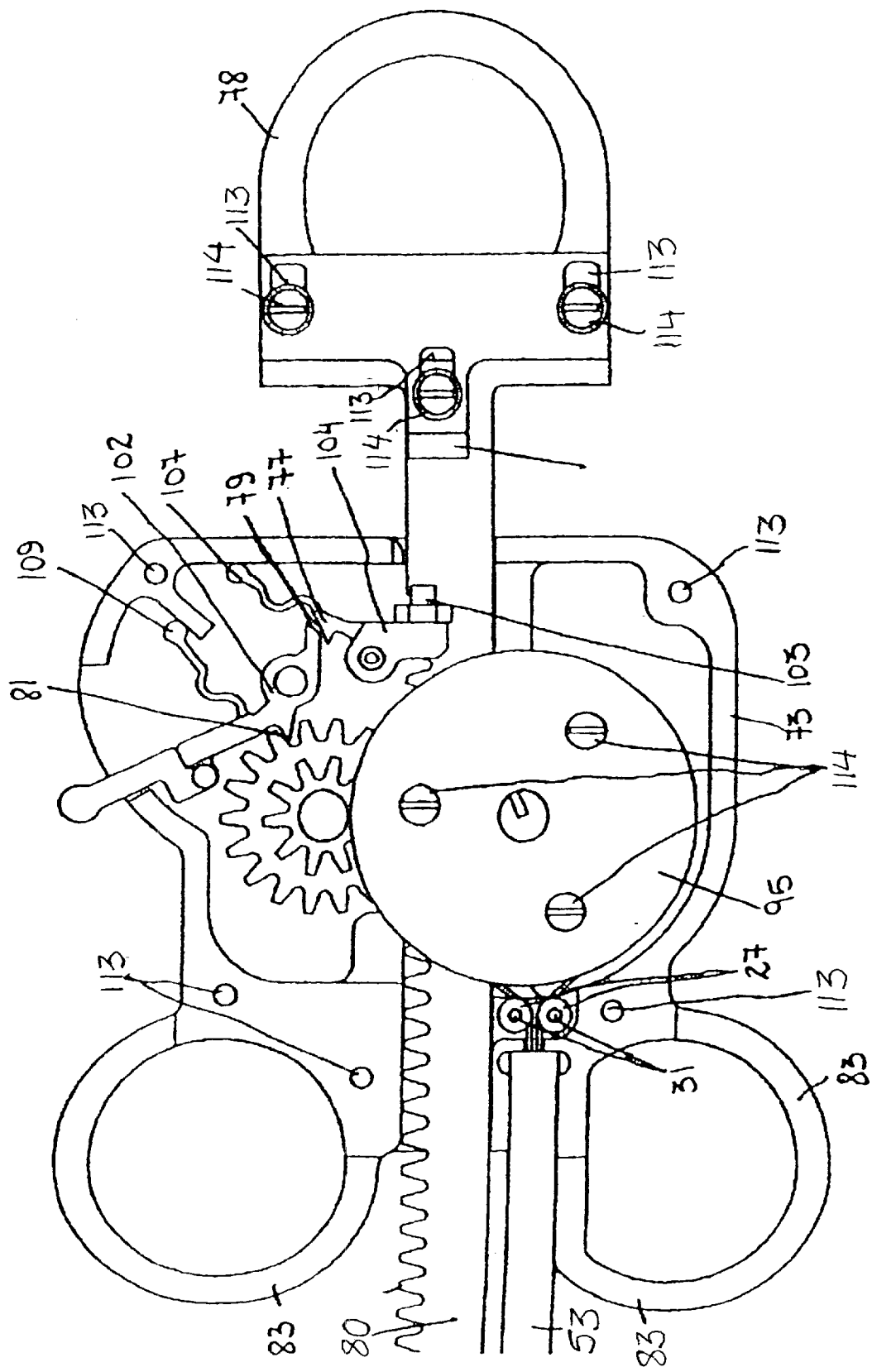
FIG. 30 is a cutaway top view of the assembled drive housing of FIGS. 25, 26 and 27 and 28 and 29 showing partial dis-engagement of the ratchet locking arm from the locking ratchet.

A typical sequence of events during use of device 20 includes placement of thimble like element 22 onto a finger of a first hand of a surgeon and insertion of the finger bearing device 20 into an intrabody location. After tactile sensing, the surgeon aligns device 20 with a location for suture placement. At this time the surgeon places at least one finger of a second hand into handle 78 of actuator 72 while stabilizing actuator 72 with one or more additional fingers placed in additional loops 83. Referring now to FIG. 28, the surgeon then begins to move handle 78 towards housing 73 so that arcuate teeth 82 of extending piece 80 engage arcuate teeth 94 of first gear 92. First gear rotates in a clockwise direction, thereby rotating second gear 96 (covered by cover 95). This causes a linear displacement of cable 100 which is translated to rotational motion 62 of rotatable wheel 58 (FIGS. 3 and 12). This rotational motion causes semi circular needle 24 to be ejected from housing 25 of thimble like element 22 via exit point 21. As handle 78 continues to move towards drive housing 73, needle 24 enters housing 25 via entry point 23. At this point distal portion 28 of needle 24 passes through loop 110 of suture 26 so that notch 44 is in proximity to suture 26. During this process, first engagement point 77 of ratchet control arm 104 engages second engagement point 79 of ratchet 102 so that third engagement point 81 of ratchet 102 does not engage arcuate teeth 94 of first gear 92. When brake 85 of brake handle 86 reaches activator 103 of ratchet control arm 104 and presses upon it, ratchet control arm 104 overcomes the tension of control arm spring 107 so that first engagement point 77 releases second engagement point 79 (FIG. 29). At this point ratchet spring 109 moves ratchet 102 so that third engagement point 81 engages at least one tooth 94 of first gear 92 thereby arresting it. This prevents further motion of second gear 96, cable 100, rotatable wheel 58 and needle 24. At this point, further progress of needle 24 is also blocked by stopping piece 67 of disc 70 According to a preferred embodiment of the present invention of device 20, the surgeon now releases finger pressure on brake handle 86 allowing spring 84 to move brake 85 away from activator 103 of ratchet control arm 104 and continues to move handle 78 away from housing 73. At this point (FIG. 30), first and second engagement points (77 and 79) are disengaged but third engagement point 81 is still holding at least one arcuate tooth of first gear 92. As handle 78 moves away from housing 73, arcuate teeth 82 impart a counterclockwise rotational motion to first gear 92. Ratchet spring 109 is now free to release third engagement point 81 of ratchet 102 from first gear 92. Counterclockwise rotational motion of first gear 92 imparts a clockwise rotational motion to second gear 96 which, as is mentioned above, is covered by cover 95. The clockwise rotational motion of second gear 96 is translated to linear displacement of cable 100 in a second direction. This reverses the direction of rotational motion 62 of rotatable wheel 58 causing withdrawal of needle 24. At this point notch 44 collects suture 26 as needle 24 is withdrawn through entry point 23 and into exit point 21, thereby placing a suture.

Figure 34A:
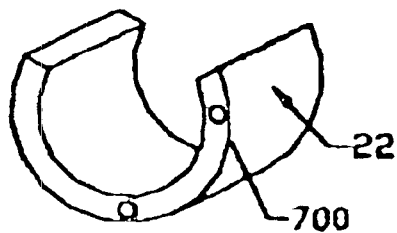
FIGS. 34a–b show a finger guided suture device according to the present invention equipped with an optical head.
Figure 34B:
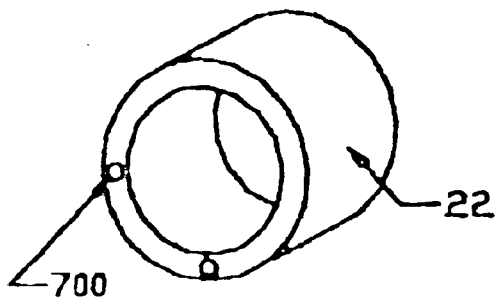

As shown, for example, in FIGS. 34a–b, according to a preferred embodiment of the present invention finger-guided suture device 20 further includes at least one optical head 700 engaged by thimble-like element 22 thereof. Optical head 700 communicates with a monitor or any other display for presenting the surgeon with details of the path to the body location to be treated or the treated body location itself prior, during or after treatment. Optical head 700 can include a miniaturized camera and/or preferably a bundle of optic-fibers to generate an image which is representable on a monitor or any other display. In addition, optical head 700 can include one or more optical elements such as, but not limited to, lenses, prisms, reflectors and the like. Of particular interest is a fish-eye lens which can be used to provide a larger field of view for optical head 700.

According to a preferred embodiment of the present invention, optical head 700 includes a lens for focusing imagery data onto a bundle of fiber optics which transmit the imagery data to a sensor, such as, but not limited to, a camera which is remote and connectable to the device or instrument. This feature is of importance in cases where the device is of a disposal type.

Finger-guided suture device 20 may further include a reporting mechanism for reporting a situation such as a full ejection of the substantially semi-circular surgical needle 24, a full withdrawal of the substantially semi-circular surgical needle 24, a degree of ejection of the substantially semi-circular surgical needle 24 or a degree of withdrawal of the substantially semi-circular surgical needle 24. The reporting mechanism may be, for example, optical head 700.

The suture device described hereinabove enjoy several important advantages over the designs described in the background section since it provides: (i) complete control of the needle motion at any time, i.e., the surgeon can retrieve the needle back to its housing at any time of the procedure without loosing the needle in the tissue; (ii) the possibility to use different types of suture material with the same needle which is realized in this case since the suture is not attached to the needle, thus allowing to load different types of suture into the cartridge and use the same needle; (iii) optimal security to the surgeon during the needle motion; (iv) optimal security to the patient since the depth of the needle bite is fixed in advanced and can not be change during the needle motion; and (v) optimal suture placement since the size of the surgical bite is fixed and known in advanced, thus the suture material can be placed in an accurate way.

The following sections relate to the use of the finger-guided suture devices herein described in various surgical procedures. It is understood that these procedures are provided as examples and are not to be taken as limiting. It will be appreciated by one ordinarily skilled in the art of surgery that many other procedures can be performed using the devices of the present invention. More particularly, the following exemplary surgical procedures describe surgical protocols in which a single finger of a surgeon is inserted intrabodily and is employed to tactile sense a body location to be treated. However, it will be appreciated that the devices of the present invention may find uses in other extra or intrabody surgical procedures.

While the suturing devices according to the invention will be described and explained herein as being applied in a novel procedure for bladder-neck suspension used for treatment of urinary incontinence (genuine stress urinary incontinence—GSUI) in females, it is also suitable for application in, e.g., sacro-spinous ligament fixation, and for anchoring suture material, even in conventional transabdominal pelvic surgery, where in obese patients exposure is limited and the surgeon has to rely on palpation of pelvic structures.

The procedure is a surgical treatment of genuine stress urinary incontinence (GSUI) in females, and aims at the correction of the suspension of the anatomical area defined as the "bladder neck", i.e., returning the bladder neck to its former, normal position. Such procedures are known, the one having the highest success rate being the Burch Colposuspension, in which the pelvic fascia and vaginal wall lateral to the urethra is suspended to Cooper's ligament. While this procedure indeed appears to be the most promising, it still is a transabdominal method, requiring general anesthesia, an extensive abdominal incision and hospitalization.

While the procedure facilitated by the present invention follows the same anatomical principles as the above-mentioned Burch method, it is, in contradistinction thereto, a transvaginal, rather than a transabdominal, bilateral suspension of the bladder neck to Cooper's ligament. It is this distinction which turns the treatment, as a matter of fact, into an office, outpatient procedure.

In cases of Rectal Prolapse, which is a known complication of Cystic Fibrosis, the surgical correction can be performed by constriction of the anal opening which might cause chronic defecation dysfunction or through an abdominal approach. In the transabdominal procedure the upper part of the rectum is anchored to the Sacral bone. Using any of the suturing devices of the present invention can render the anchoring procedure in the small and deep pelvic area an easier and shorter process, avoiding the need of extensive dissection to expose the correct anatomical target.

Another procedure that will benefit from the use of the suturing devices of the present invention is in the case of treating Esophageal reflux in children. The surgical correction is based on reconstruction of a one way valve mechanism around the Esophagus. Passing a "Vessel loop", i.e., a thin rubber band, around the Esophagus prevents the reflux. Any of the suturing devices of the present invention can replace the need for dissection of the Esophagus and makes it easy to pass the Vessel loop behind the esophagus in a short and safe fashion.

Normal vaginal delivery exposes the female pelvic floor to muscle and connective tissue trauma which in some cases results in pelvic floor relaxation and pelvic organ prolapse. Vaginal prolapse is a result of weakening of connective tissue support to the vaginal vault apex. One of the most common surgical techniques used to correct vaginal prolapse includes tying the upper part of the vagina to a connective tissue condensation stretched from both sides of the sacrum. This anatomical structure is called The Sacrospinous Ligament, and the procedure is called Sacrospinous Ligament Fixation. In order to perform the procedure, the surgeon needs to open the posterior wall of the vagina and enter to a space beside the rectum to reach the ligament. A surgical thread is anchored to the ligament and is thereafter tied to the vagina, thus fixing the upper part of the vagina to the ligament. Since the location of the ligament is deep in the pelvic hole, the surgeon needs to perform extensive dissection to expose the ligament and place the suture material under direct visualization using long instruments. However, palpation of the ligament is easy and within reach of the surgeon's finger. Mounting any of the suturing devices according to the present invention over the surgeon's finger thus enables the surgeon to place the suture in the correct location, avoiding the need for extensive dissection, reducing blood lose and shortening operation time. Palpation of the correct location makes the procedure even safer by reducing the risk of injury to pelvic blood vessels behind certain areas of the ligament.

Rupture of the rectum in large animals, especially horses and cows, oftentimes happens during rectal examination when a peristaltic wave passes over the wrist of the examiner, or following insertion of a stallion's penis into the rectum. Usually a colostomy is done to bypass the rectum and then an attempt is made to suture the tear in the rectum at a distance of 30 to 40 cm from the anus. The suture is placed blindly by palpation of the tear and an attempt is made to place a suture using a needle held by the finger of the operator. Any of the suturing devices according the present invention can be employed to assist suturing the tear.

Injury to the cervix after foaling is a known complication. This leads to infertility because of loss of the fetus through the cervix 1 to 3 months after conception. The present treatment involves placement of sutures into the cervix after conception, so as to reduce the size of the opening. These sutures are inserted blindly by a needle held by the fingers. Any of the suturing devices according to the present invention can be used instead.

In cases of rupture of the uterus at parturition, often the tear is large and repair must be done by means of a laparotomy. However, a small tear can be caused by a foot of the foal. Present treatment is effected by placing sutures in the uterus after parturition. These sutures close the small openings and prevent rupture of the uterus in the next pregnancy. Presently, these sutures are placed blindly by a needle held by the fingers. Any of the suturing devices according to the present invention can be used instead.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A finger-guided suture device, comprising:
   (a) a thimble-like element being adapted to surround a portion of a surgeon's finger;
   (b) a rotatably mounted, substantially semi-circular surgical needle within a housing formed within, or connected to, a wall of said thimble-like element, said surgical needle being designed for collecting said surgical suture via a distal portion of said surgical needle upon contact therewith and for retaining and guiding said surgical suture while suturing; and
   (c) a mechanism for imparting to said surgical needle a rotary movement in one direction for ejecting said surgical needle from said thimble-like element and thereafter a rotary movement in the opposite direction for withdrawing said surgical needle into said thimble-like element, so as to place a suture.

2. The finger-guided suture device of claim 1, wherein said thimble like element is designed and constructed to expose the ventral tactile portions of the distal phalanx of said surgeon's finger, so as to enable said surgeon to tactile sense a body location to be sutured.

3. The finger-guided suture device of claim 1, further comprising:
   (d) a cartridge for holding said surgical suture and presenting it for collection by said distal portion of said surgical needle.

4. The finger-guided suture device of claim 3, wherein said cartridge includes at least one mechanism designed and constructed, so as to maintain a predetermined tension of said surgical suture.

5. The finger-guided suture device of claim 4, wherein said at least one mechanism designed and constructed, so as to maintain a predetermined tension of said surgical suture comprises at least one piece of flexible material containing at least one hole through which said surgical suture passes.

6. The finger-guided suture device of claim 5, wherein said at least one piece of flexible material containing at least one hole is selected from the group consisting of a single piece of flexible material containing two holes and a pair of pieces of flexible material each containing one hole.

7. The finger-guided suture device of claim 5, wherein said flexible material is selected from the group consisting of silicon, latex, rubber, fabric, and fabric with an eyelet.

8. The finger-guided suture device of claim 7, wherein said eyelet is constructed of material selected from the group consisting of silicon, latex, rubber and fabric.

9. The finger-guided suture device of claim 1, wherein said mechanism for ejecting said surgical needle from, and withdrawing said surgical needle into, said thimble-like element, is selected from the group consisting of a belt actuated mechanism, a gear actuated mechanism and a combined gear and belt actuated mechanism.

10. The finger-guided suture device of claim 1, wherein said surgical needle is formed with a feature selected from the group consisting of a notch, a hook, at least one arm, and an openable loop at said distal end thereof.

11. The finger-guided suture device of claim 1, further comprising an adapter insertable between said thimble-like element and the surgeon's finger, so as to adapt the suture device to fingers of different size.

12. The finger-guided suture device of claim 1, wherein said mechanism includes a first portion engaged within said housing and which is in contact with said ejectable surgical needle and a second, remote, portion which is to extend out of the patient's body and which is operable by a free hand of the surgeon so as to eject said surgical needle from said thimble-like element.

13. The finger-guided suture device of claim 12, wherein said first portion of said mechanism comprises a rotatable wheel having an axle, said axle serves for engaging said surgical needle and imparting a rotational motion in at least one direction thereto, said surgical needle includes a mechanism for engaging said rotatable wheel and a locking piece for insuring that said surgical needle and said rotatable wheel remain engaged.

14. The finger-guided suture device of claim 12, wherein said first portion of said mechanism comprises a rotatable wheel having a mechanism for engaging a drive arm and imparting a rotational motion in at least one direction thereto, said drive arm is designed and constructed engageable by said rotatable wheel and by said surgical needle and to impart a rotational motion of said rotatable wheel in at least one direction to said surgical needle, wherein said surgical needle further includes a mechanism for engaging said drive arm and a disk for ensuring that said surgical needle, said drive arm and said rotatable wheel remain engaged.

15. The finger-guided suture device of claim 12, wherein said remote portion which is to extend out of the patient's body and which is operable by a free hand of the surgeon so as to eject said surgical needle from said thimble-like element comprises:
   (i) a hand operable actuator designed and constructed to operate a drive mechanism;
   (ii) a drive housing for containing at least a portion of said drive mechanism; and
   (iii) at least a portion of said drive mechanism, said drive mechanism being for imparting a rotational motion in at least one direction to said surgical needle.

16. The finger-guided suture device of claim 15, wherein said hand operable actuator of said remote portion comprises:
   (1) a handle for engaging at least one finger of said free hand of said surgeon;

(2) an extending piece containing a plurality of arcuate teeth and being movable through said drive housing;

(3) a pressure sensitive spring; and (4) a brake handle, said brake handle operable in a first direction by said pressure sensitive spring and in a second direction by said at least one finger of said free hand of said surgeon.

17. The finger-guided suture device of claim 15, wherein said drive mechanism comprises:

(1) a plurality of arcuate teeth deployed in a linear arrangement along an extending piece of a handle;

(2) a first gear with a first circular arrangement of arcuate teeth, said first circular arrangement of arcuate teeth being for engaging with said plurality of arcuate teeth deployed in said linear arrangement along said extending piece, such that linear displacement of said extending piece is translated into rotational motion of said first gear;

(3) a second gear including a second circular arrangement of arcuate teeth, said arcuate teeth of said second gear being for engaging said first circular arrangement of arcuate teeth of said first gear, such that rotational motion of said first gear causes rotational motion of said second gear; and (4) a cable in contact with at least one point on said second gear, such that rotational motion of said second gear is translated to linear motion of at least a portion of said cable.

18. The finger-guided suture device of claim 17, wherein said drive mechanism further comprises:

(5) a ratchet for alternately engaging and releasing at least one arcuate tooth of said first gear;

(6) a ratchet control arm for alternately engaging and releasing said ratchet;

(7) a brake handle for alternately operating said ratchet control arm;

wherein, when said brake handle operates said ratchet control arm, said ratchet control arm releases said ratchet, said ratchet engages said at least one arcuate tooth of said first gear and said first gear is prevented from rotating; and whereas, when said brake handle does not operate said ratchet control arm, said ratchet control arm engages said ratchet, said ratchet releases said at least one arcuate tooth of said first gear and said first gear is free to rotate.

19. The finger-guided suture device of claim 1, wherein said thimble-like element is constructed so as to be mounted over a dorsal side of the distal phalanx of said surgeon's finger, thereby exposing the entire ventral tactile portions of the distal phalanx.

20. The finger-guided suture device of claim 1, wherein said thimble-like element is constructed so as to fully surround the distal phalanx and expose the tip of the ventral tactile portion of the distal phalanx.

21. The finger-guided suture device of claim 1, wherein said thimble-like element is constructed so as to be mounted over a ventral side of the distal phalanx of the surgeon's finger and expose the tip of the ventral tactile portion of the distal phalanx.

22. The finger-guided suture device of claim 1, wherein said surgical needle is ejectable in a direction generally perpendicular to a longitudinal axis of said thimble like element.

23. The finger-guided suture device of claim 1, wherein said surgical needle travels along at least a portion of a circular path, said path being on a plane which substantially parallels a plane traversing the surgeon's finger from top to bottom.

24. The finger-guided suture device of claim 1, wherein said surgical needle travels along at least a portion of a circular path, said path being on a plane which substantially parallels the surgeon's finger from side to side.

25. The finger-guided suture device of claim 1, wherein said surgical needle travels along at least a portion of a circular path, said path being on a plane which is substantially perpendicular to the longitudinal axis of the surgeon's finger.

26. The finger-guided suture device of claim 1, further comprising an optical head engaged by said thimble like element.

27. The finger-guided suture device of claim 1, further comprising said surgical suture formed with a loop for collection by said surgical needle.

28. The finger-guided suture device of claim 1, wherein said wall is a side wall of said thimble-like element.

29. The finger-guided suture device of claim 1, wherein said wall is a front wall of said thimble-like element.

30. The finger-guided suture device of claim 1, further comprising a reporting mechanism for reporting at least one situation selected from the group consisting of a full ejection of said substantially semi-circular surgical needle, a full withdrawal of said substantially semi-circular surgical needle, a degree of ejection of said substantially semi-circular surgical needle and a degree of withdrawal of said substantially semi-circular surgical needle.

31. A surgical procedure for bladder-neck suspension for treatment of urinary incontinence, the procedure comprising the step of suspending a pelvic fascia and a vaginal wall lateral to a urethra of a patient to Cooper's ligament by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

32. A surgical procedure for treatment of rectal prolapse, the procedure comprising the step of constricting an anal opening by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

33. A surgical procedure for treatment of esophageal reflux, the procedure comprising the step of positioning a vessel loop around a esophagus of a patient by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

34. A surgical procedure for treatment of vaginal prolapse, the procedure comprising the step of tying an upper part of a vagina of a patient to a sacrospinous ligament of the patient by a surgical suture applied by using a finger-guided suture device having rotatably-driven, substantially semi-circular surgical needle designed for collecting said surgical suture via a distal portion of said surgical needle upon contact therewith and for retaining and guiding said surgical suture while suturing.

35. A surgical procedure for treatment of rupture of a rectum in large animals, the procedure comprising the step of suturing the rupture by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

36. A surgical procedure for treatment of rupture of a cervix in large animals, the procedure comprising the step of suturing the rupture by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

37. A surgical procedure for treatment of rupture of a uterus in large animals, the procedure comprising the step of suturing the rupture by a surgical suture applied by using a finger-guided suture device having a rotatably-driven, substantially semi-circular surgical needle designed for collecting said surgical suture via a distal portion of said surgical needle upon contact therewith and for retaining and guiding said surgical suture while suturing.

* * * * *